US011202917B2

(12) United States Patent
Rutledge et al.

(10) Patent No.: US 11,202,917 B2
(45) Date of Patent: Dec. 21, 2021

(54) MEDICAL DEVICE WITH CAM BASED ROTATING FASTENER

(71) Applicant: Medtronic, Inc., Minneapolis, MN (US)

(72) Inventors: Don A. Rutledge, Corcoran, MN (US); Greg J. Doyle, White Bear Lake, MN (US)

(73) Assignee: Medtronic, Inc, Minneapolis, MN (US)

( * ) Notice: Subject to any disclaimer, the term of this patent is extended or adjusted under 35 U.S.C. 154(b) by 75 days.

(21) Appl. No.: 16/712,360

(22) Filed: Dec. 12, 2019

(65) Prior Publication Data
US 2021/0178167 A1 Jun. 17, 2021

(51) Int. Cl.
*A61N 1/375* (2006.01)
(52) U.S. Cl.
CPC .................. *A61N 1/3754* (2013.01)
(58) Field of Classification Search
CPC ................ A61N 1/3754; A61N 1/3605; A61N 1/36062; A61N 1/37235; A61N 1/37247; A61N 1/3752; H01R 2201/12; H01R 4/5008; H01R 13/5224
See application file for complete search history.

(56) References Cited

U.S. PATENT DOCUMENTS

| | | | |
|---|---|---|---|
| 4,860,750 A | 8/1989 | Frey et al. | |
| 5,766,042 A | 6/1998 | Ries et al. | |
| 5,951,595 A | 9/1999 | Moberg et al. | |
| 6,609,029 B1 | 8/2003 | Mann et al. | |
| 6,741,892 B1* | 5/2004 | Meadows | A61N 1/3752 607/116 |
| 8,301,255 B2 | 10/2012 | Barker | |
| 9,381,367 B2 | 7/2016 | Janzig | |
| 2003/0003787 A1 | 1/2003 | Bakker et al. | |
| 2007/0169524 A1* | 7/2007 | Tharp | F16K 24/04 70/172 |
| 2009/0233491 A1 | 9/2009 | Barker et al. | |

(Continued)

FOREIGN PATENT DOCUMENTS

WO 2015061445 A1 4/2015

OTHER PUBLICATIONS

International Search Report and Written Opinion of International Application No. PCT/US2020/064313, dated Mar. 3, 2021, 14 pp.

*Primary Examiner* — Mallika D Fairchild
(74) *Attorney, Agent, or Firm* — Shumaker & Sieffert, P.A.

(57) ABSTRACT

In one example, a medical device includes a housing having a channel configured to receive an electrical lead. The medical device can further have a rotatable member having a longitudinal axis about which the rotatable member is configured to rotate. The rotatable member can have an outer surface having a first radius from the longitudinal axis. The rotatable member can also have a cam lobe extending farther from the longitudinal axis than the first radius of the outer surface. The cam lobe can have a substantially planar surface parallel to the longitudinal axis. The substantially planar surface of the cam lobe can be configured to retain the electrical lead within the channel. The medical device can further have a slider having a central portion substantially parallel with the cam lobe. The slider can further have a slider protrusion on the central portion of the slider.

20 Claims, 18 Drawing Sheets

(56) References Cited

U.S. PATENT DOCUMENTS

| | | | |
|---|---|---|---|
| 2009/0270940 A1* | 10/2009 | Deininger | A61N 1/3752 607/37 |
| 2010/0261362 A1* | 10/2010 | Boyd | H01R 13/514 439/271 |
| 2011/0039445 A1* | 2/2011 | Boyd | H01R 13/5224 439/490 |
| 2011/0270018 A1* | 11/2011 | Honaryar | A61F 5/005 600/37 |
| 2012/0245657 A1* | 9/2012 | Lim | A61N 1/3752 607/72 |

* cited by examiner

MEDICAL DEVICE WITH CAM BASED ROTATING FASTENER

TECHNICAL FIELD

The disclosure is related to medical devices, and more specifically, devices, systems, and techniques for temporarily securing elongated members to medical devices.

BACKGROUND

Medical devices, which included external or implantable medical devices (IMDs), may be used to treat a variety of medical conditions. Some medical devices may be attached to medical leads for sensing and/or delivery of electrical stimulation therapy to a patient via implanted electrodes. For example, an implantable electrical stimulation device may include an electrical stimulation generator and be attached to one or more implantable leads carrying one or more electrodes. In some cases, implantable electrodes may be coupled to an external medical device including an electrical stimulation generator via one or more percutaneous leads or fully implanted leads.

Example IMDs may be configured to function as neurostimulators, cardiac monitors, cardiac defibrillators, cardiac pacemakers and others. Electrical stimulation therapy may include stimulation of nerve, muscle, or brain tissue or other tissue within a patient. An electrical stimulation device may be fully implanted within the patient. Medical electrical stimulators have been proposed for use to relieve a variety of symptoms or conditions such as heart disease, chronic pain, tremor, Parkinson's disease, depression, epilepsy, migraines, urinary or fecal incontinence, pelvic pain, sexual dysfunction, obesity, and gastro paresis. An electrical stimulator may be configured to deliver electrical stimulation therapy via medical leads carrying electrodes implantable proximate to the heart, spinal cord, pelvic nerves, gastrointestinal organs, peripheral nerves, or within the brain of a patient. Stimulation proximate the spinal cord, within the brain, and proximate peripheral nerves are often referred to as spinal cord stimulation (SCS) deep brain stimulation (DBS), and peripheral nerve stimulation (PNS), respectively.

SUMMARY

This disclosure includes devices, systems, and techniques for securing the proximal end of a medical lead to an IMD with a fastener device incorporating a rotating member having a cam lobe. The cam lobe may be formed to have a substantially planar surface configured to contact the medical lead. For example, rotation of the rotating member can cause the substantially planar surface of the cam lobe to be disposed against the medical lead and provide a bias force resisting linear movement of the medical lead. In some examples, the rotating member and cam lobe can be used to impart a linear motion to a slider, intermediary impinger, or spring, which in turn is disposed against the medical lead providing a bias force resisting linear movement.

In one example, a medical device includes a housing having a channel configured to receive an electrical lead. The medical device can further have a rotatable member having a longitudinal axis about which the rotatable member is configured to rotate. The rotatable member can have an outer surface having a first radius from the longitudinal axis. The rotatable member can also have a cam lobe extending farther from the longitudinal axis than the first radius of the outer surface. The cam lobe can have a substantially planar surface parallel to the longitudinal axis. The substantially planar surface of the cam lobe can be configured to retain the electrical lead within the channel. The rotatable member can further have a lever extending from the rotatable member perpendicular to the longitudinal axis. The medical device can further have a slider having a central portion substantially parallel with the cam lobe. The central portion can terminate in a first end and a second end where both the first end and the second end extend away from the channel. The slider can further have a slider protrusion on the central portion of the slider. The slider protrusion can have a substantially planar surface parallel to the channel. The slider protrusion can be configured to engage the electrical lead as the rotatable member is rotated toward the center portion. The slider can further have a cam stop operably coupled to the first end and extending inward toward the rotatable member, substantially parallel with the first end. The cam stop can be configured to contact and restrict rotation of the rotatable member when the cam lobe engages the cam stop. The slider can further have a retraction member operably coupled to the second end and extending toward the rotatable member substantially parallel to the channel. The retraction member can be configured to contact the cam lobe during rotation of the cam lobe in a retraction direction. The cam lobe can be configured to engage the retraction member as the slider is pulled away from the channel.

In another example, a medical system having a medical device including a housing with a first channel configured to receive a first electrical lead. The medical device further can have a first rotatable member with a longitudinal axis about which the first rotatable member is configured to rotate. The first rotatable member can have an outer surface having a first radius. Further, the rotatable member can have a cam lobe extending farther from the longitudinal axis than the first radius of the outer surface. The cam lobe can have a substantially planar surface parallel to the longitudinal axis. The substantially planar surface of the cam lobe can be configured to retain the first electrical lead within the first channel. The medical device housing can further have a second channel defined by the housing configured to receive a second electrical lead and have a second rotatable member having a longitudinal axis about which the second rotatable member is configured to rotate. The second rotatable member can also have an outer surface having a first radius. The second rotatable member can also have a cam lobe extending farther from the longitudinal axis than the first radius of the outer surface. The cam lobe can have a substantially planar surface parallel to the longitudinal axis. The substantially planar surface of the cam lobe is configured to retain the second electrical lead within the second channel. The medical device can further have a first slider substantially encompassing the first rotatable member. The first slider is slidably mounted and configured to slide toward the first channel as the rotatable member rotates the cam lobe towards a central portion of the first slider. The central portion can be substantially parallel with the first channel. The first slider can have a retraction member located opposite of the central portion across from the rotatable member and substantially parallel to the central portion. The cam lobe can be configured to engage the retraction member as the cam lobe is rotated away from the central portion to move the slider away from the first channel. The medical device can further have a stimulation generator configured to generate electrical stimulation deliverable via one or more electrodes of the electrical lead.

In another example, a medical device having a housing with a channel configured to receive an electrical lead and a chamber adjacent to the channel. The medical device can further have a rotatable member located within the chamber. The rotatable member can have an outer surface having a first radius and a cam lobe extending farther from the first radius of the outer surface. The cam lobe can have a substantially planar surface parallel to the longitudinal axis. The medical device can further have a slider having a central portion substantially parallel with the cam lobe. The central portion can terminate in a first end and a second end where both the first end and the second end extend away from the channel. The slider can be configured to slide into contact with the electrical lead and secure the electrical lead within the channel. The cam lobe can be configured so as the rotatable member is rotated and the cam lobe engages the central portion of the slider, it pushes on the central portion to move the slider toward the channel. The slider can further have a slider protrusion on the central portion of the slider. The slider protrusion can have a substantially planar surface parallel to the channel. The slider protrusion can be configured to engage the electrical lead as the rotatable member is rotated toward the center portion. The slider can further have a cam stop operably coupled to the first end and extending inward toward the rotatable member, substantially parallel with the first end. The cam stop can be configured to contact and restrict rotation of the rotatable member when the cam lobe engages the cam stop. The slider may further have a retraction member operably coupled to the second end and extending toward the rotatable member substantially parallel to the channel. The retraction member can be configured to contact the cam lobe during rotation of the cam lobe in a retraction direction. The cam lobe can be configured to engage the retraction member as the slider is moved away from the channel.

The details of one or more examples of this disclosure are set forth in the accompanying drawings and the description below. Other features, objects, and advantages of this disclosure will be apparent from the description and drawings, and from the claims.

BRIEF DESCRIPTION OF DRAWINGS

FIGS. 11A, 11B, 11C, 1D, 11E, 11F, 11G, 11H and 11I are conceptual diagrams illustrating an example device and technique for securing a medical lead to an IMD with a rotatable member.

DETAILED DESCRIPTION

Figure 1:
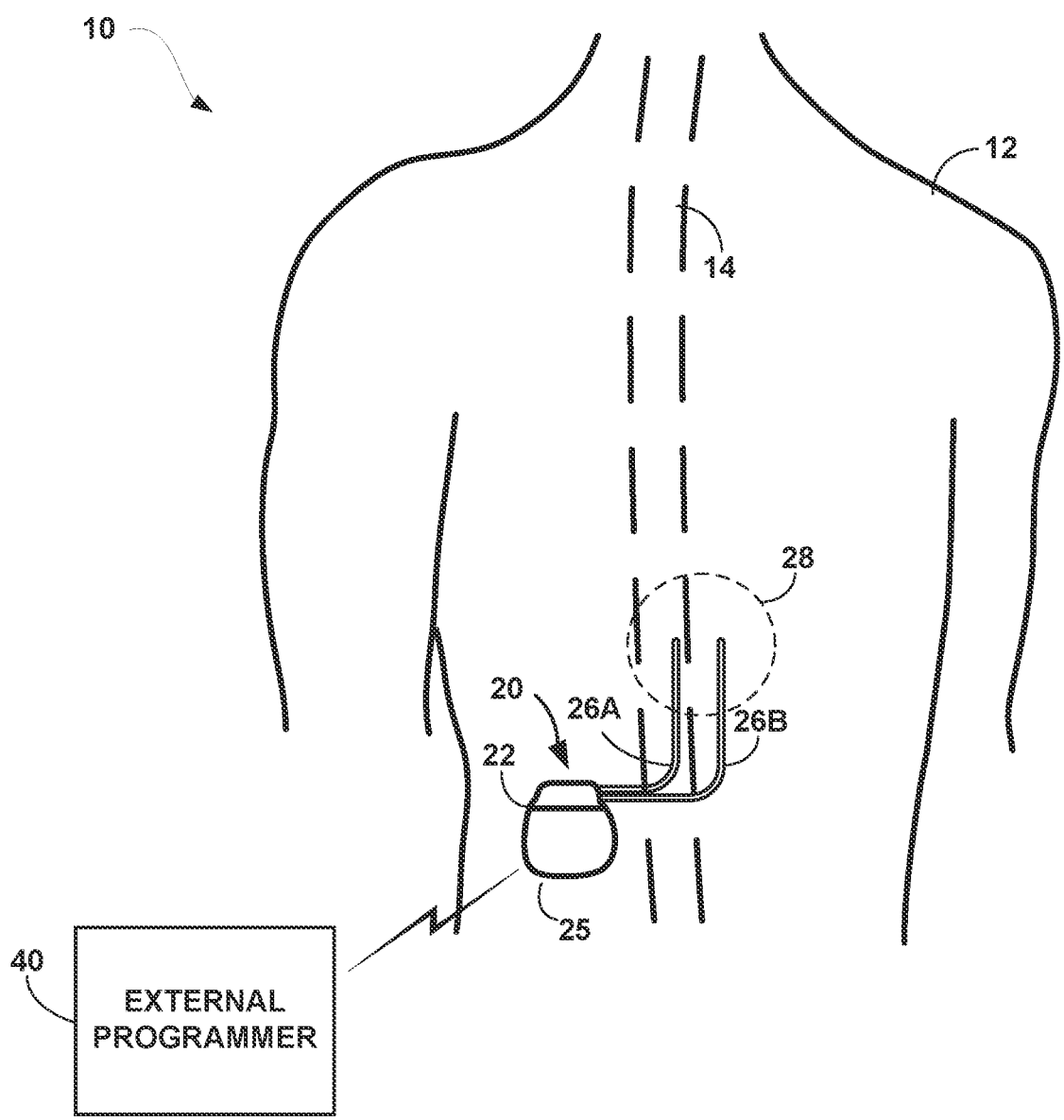
FIG. 1 is a conceptual diagram of a medical system including an IMD with medical leads configured to deliver gastric stimulation therapy.

This disclosure includes devices, systems, and techniques for securing the proximal end of a medical lead to a medical device, such as an IMD, with a cam based rotating fastener device. To retain a lead (or drug catheter in other examples) in an IMD, the IMD may utilize a set screw, which when advanced toward the lead, applies a force directly to the side of the lead housing or metal band around the housing of the lead. Friction forces and/or deformation caused by the set screw may prevent the lead from being pulled out from the IMD. The depth and force of the set screw is determined by the physician manually rotating the screw. However, if the physician over rotates the set screw, the force applied to the lead from the set screw may deform the lead and cause damage to the lead housing and/or elements within the lead, such as one or more electrical conductors. A damaged lead may need to be replaced or, if not replaced, prevent full operation of the medical device and/or lead.

As described herein, a cam lobe on the side of a rotatable member of a fastener may be configured to applying a force directly to the side of a lead with a limited distance the cam lobe can travel towards the side of the lead. The cam lobe may also define a substantially planar surface contacting the side of the lead to secure the lead and resist movement of the cam lobe due to axial force from the lead. This cam lobe thus avoids potential deformation of the lead. The cam fastener can also provide a very low-profile height compared to a set screw since it operates on the side of the cable rather than the top. Further, a portion of the set screw height is the additional needed height for movement (e.g., the extra rotational movement needed) and a retaining feature above the screw threads). A rotatable member's height of examples described below can be anywhere from 0.040 inches (1.02 mm) to 0.060 inches (1.52 mm) smaller than a set screw. Further, the rotatable member does not stick out away from the implantable device, thus creating a smooth profile for a flush profile surface. In one example, the volume occupied by rotatable member is, 0.0023 cubic inches (0.0377 cubic cm), which may be comparable to or less than set screws, which may be used to retain a lead in other examples. Even when the rotatable member is used in combination with an intermediate member the volume occupied may be between 0.002 and 0.003 cubic inches (0.032 and 0.049 cubic cm) in some examples.

The cam lobe shape provides a positive engagement feel for the implanting physician, has a low assembly height and provides permanent fastener retention. The substantially planar surface helps prevent any deformation from over rotation of a set screw. The force applied by the cam lobe is not dependent on the implanting physician, but instead is dependent upon whether the cam lobe is engaged with the lead or not. The substantially planar surface provides a "locking", "anti-rotation", or "resting position" action provided by the lobe's "substantially planar surface". The medical lead elastically deforms and provides a spring back return force to the lobe's planar surface. The elastic deformation force would need to be overcome for the cam to be turned out of its resting (locked) position.

Further, the cam shape cannot crush the implantable lead because the cam lobe has a fixed distance it extends toward the lead. Furthermore, an intermediate member can be added between the cam member and the lead to control the contact area and secure leads without axial force or movement. The intermediate member can be used to prevent abrasion to the lead as the intermediate member does not move or rotate as the rotatable member does. A rotatable cam provides simple operation, can be configured for standard tools (e.g., an Allen® wrench (or hex key), slotted screwdriver, hand operated lever, etc.) and can provide visual cues for the physician installing the IMD.

As described herein, a connector block may be referred to as a header of the IMD in some examples. Structures for retaining a medical lead may include actuatable cam mechanisms configured to mechanically connect a medical lead to an IMD. Such a flexible clamping mechanism may be located adjacent, near or next to channels configured to receive the proximal end of a medical lead. Actuating the rotatable cam mechanism may apply a compressive force to a medical lead in the proximal end of the medical lead, thereby mechanically connecting the medical lead to the rotating cam member.

For purposes of this disclosure the term "substantially" when used in relation to describing elements, shall be defined as being largely and or wholly the item specified. When used in relation to quantities, it can mean considerable in quantity; significantly great.

FIG. 1 illustrates an example medical system 10 including an IMD 20 with a medical lead(s) 26A, 26B (hereinafter referred to collectively as leads 26 or leads 26A, 26B, 26C, 26D) configured to deliver therapy. IMD 20 is configured to deliver therapy to patient 12 through medical leads 26. Medical lead(s) 26 are connected to IMD 20 by connector block 22. In some references, a connector block, such as connector block 22, is instead referred to as a header of the IMD. In any event, connector block 22 provides the means for forming an electrical connection between electrical contacts of medical lead 26 and feedthrough pins of feedthroughs passing through the housing of IMD 20, which forms a hermetically sealed enclosure for the electronic components of IMD 20. In other examples, a portion of IMD 20 may accept a lead and provide electrical contact with a hermetic seal without being arranged as a separate header or connector block.

IMD 20 may include a power source as well as processing circuitry, microprocessors, internal memory, and other electronic circuitry for executing software or firmware to provide the functionality described herein. The software executing thereon may perform a variety of sensing, diagnostic, and/or therapy-related operations, one such therapy operation may be stimulation of spinal cord 14 through medical lead 26 operatively (i.e. electrically and/or mechanically) connected to IMD 20 by connector block 22.

Connector block 22 is configured to receive the proximal end of medical lead 26. Connector block 22 includes one or more fasteners with actuatable clamps, such as fastener device 24 (shown in FIG. 5), which are configured to secure the proximal end of one or more medical leads 26 to IMD 20.

Medical system 10 further includes external programmer 40. In different examples, external programmer 40 may include an external medical device, a programming device, a remote telemetry station, a physician-activated device, a patient-activated device, a display device or any other type of device capable of sending and receiving signals to and from IMD 20. In some implementations, IMD 20 generates content to display on external programmer 40. In other implementations, external programmer 40 communicates instructions to IMD 20 based on the content received from a cloud server, a computer system, and/or a mobile device.

As described herein, IMD 20, and the software executing thereon, provides a platform for providing therapy to spinal cord 14 through medical lead(s) 26. For example, IMD 20 may be configured to receive and process electrical signals produced by the body of patient 12 using medical lead(s) 26. IMD 20 may also use medical lead(s) 26 to deliver therapy, such as SCS therapy, to spinal cord 14 of patient 12. In other examples, one or more medical leads 26 may be dedicated by IMD 20 to receive electrical signals, and one or more other medical leads 26 may be dedicated to delivering therapy to spinal cord 14 of patient 12.

In some examples, IMD 20 may implement techniques for automated receiving and processing of electrical signals indicating a need for therapy. For example, IMD 20 may allow a user, by communicating with external programmer 40, control over one or more therapy techniques used by IMD 20 in response to IMD 20 receiving and processing electrical signals from medical lead 26 indicating a need for treatment. In another example, a user may use external programmer 40 to provide pre-determined responses for therapy through medical lead 26 to respond to IMD 20 receiving and processing electrical signals from medical lead 26 indicating a need for treatment.

In the example of FIG. 1, IMD 20 is illustrated as an IMD for providing therapy to a spinal cord. However, in other examples, IMD 20 may be configured to function as a neurostimulator, cardiac monitor, cardiac defibrillator, cardiac pacemakers, or any other type of simulation and/or sensing device utilizing one or more medical leads.

As described herein, IMDs deliver therapy through one or more medical leads 26A, 26B based on external programmer 40 and/or internal programming for software which, as described, can efficiently deliver therapy to targeted areas. In this example, connector block 22 may be the result of multiple components.

Medical leads 26A, 26B may include one or more electrodes. In the example illustrated, medical leads 26A, 26B may each include a respective tip electrode and ring electrode located near a distal end of their respective medical leads 26A, 26B. When implanted, the tip electrodes and/or the ring electrodes are placed relative to or in a selected tissue, muscle, nerve or other location within the patient.

Medical leads 26A, 26B are connected at a proximal end to IMD 20 by connector block 22. Connector block 22 may include one or more fasteners, such as fastener device 24 (see FIG. 5) interconnecting with one or more contact rings located on the proximal end of medical leads 26A, 26B. Medical leads 26A, 26B are operatively connected to one or more of the electrical components within housing 25. One or more conductors (not shown) extend within medical leads 26A, 26B from the contact rings along the length of the medical lead to engage the ring electrode and the tip electrode respectively. In some examples, medical leads 26A, 26B may each include a plurality of ring electrodes, such as four or eight electrodes. For example, DBS therapy may utilize medical leads including four ring electrodes, whereas SCS therapy may utilize medical leads including eight ring electrodes. In other examples, leads 26A, 26B may include a complex electrode array which may include electrodes at the same axial position on the lead but at different respective circumferential positions around the lead. These electrodes at different circumferential positions may be provided alone, or in combination with one or more ring electrodes, a tip electrode, or other types of electrodes on each lead. In any case, each of the tip electrodes (if present) and the ring electrodes are operatively coupled to a respective conductor within its associated medical lead bodies. For example, a first electrical conductor can extend along the length of the body of medical lead 26A from connector block 22 and operatively couple to the tip electrode and a second electrical conductor can extend along the length of the body of medical lead 26A from connector block 22 and operatively couple to the ring electrode. The respective conductors may be operatively coupled to circuitry, such as a stimulation generator 34 as described in FIG. 3, of IMD 20 via connections in connector block 22.

In different examples, stimulation 28 may instead include peripheral nerve stimulation (PNS) or peripheral nerve field stimulation (PNFS) therapy, and/or any other stimulation provided by a neurostimulator, a cardiac monitor, a cardiac defibrillator, a cardiac pacemaker, or any other type of mobile or non-mobile computing device suitable for performing the techniques described herein.

IMD 20 may also provide sensing functions in addition to or alternatively to stimulation functions. For example, IMD 20 may be configured to receive and process electrical signals produced by the body of patient 12 using medical leads 26A, 26B to indicate a need for therapy. After a need for therapy is detected by IMD 20, IMD 20 may respond by using medical leads 26A, 26B to deliver therapy, such as stimulation 28, to the body of patient 12. In other examples, one or more medical leads 26A, 26B may be dedicated by IMD 20 to receiving electrical signals and/or delivering therapy, such as stimulation 28 to the body of patient 12.

IMD 20 is illustrated as an IMD for providing therapy to the torso of patient 12. However, in other examples, IMD 20 may be a neurostimulator, cardiac monitor, cardiac defibrillator, cardiac pacemaker or any other type of mobile or non-mobile computing device suitable for performing the techniques described herein.

Housing 25 of IMD 20 can be constructed of conductive materials, non-conductive materials or a combination thereof. As described herein, housing 25 of IMD 20 may provide a substantially sealed environment for processing circuitry, memories, transmitters, receivers, transceivers, sensors, sensing circuitry, therapy circuitry, antennas, power sources, and other components of IMD 20. In the example of FIG. 1, IMD 20 delivers therapy through one or more medical leads 26A, 26B connected operatively to IMD 20 by connector block 22 utilizing one or more fasteners, such as fastener device 24 as described in FIG. 5.

Figure 3:
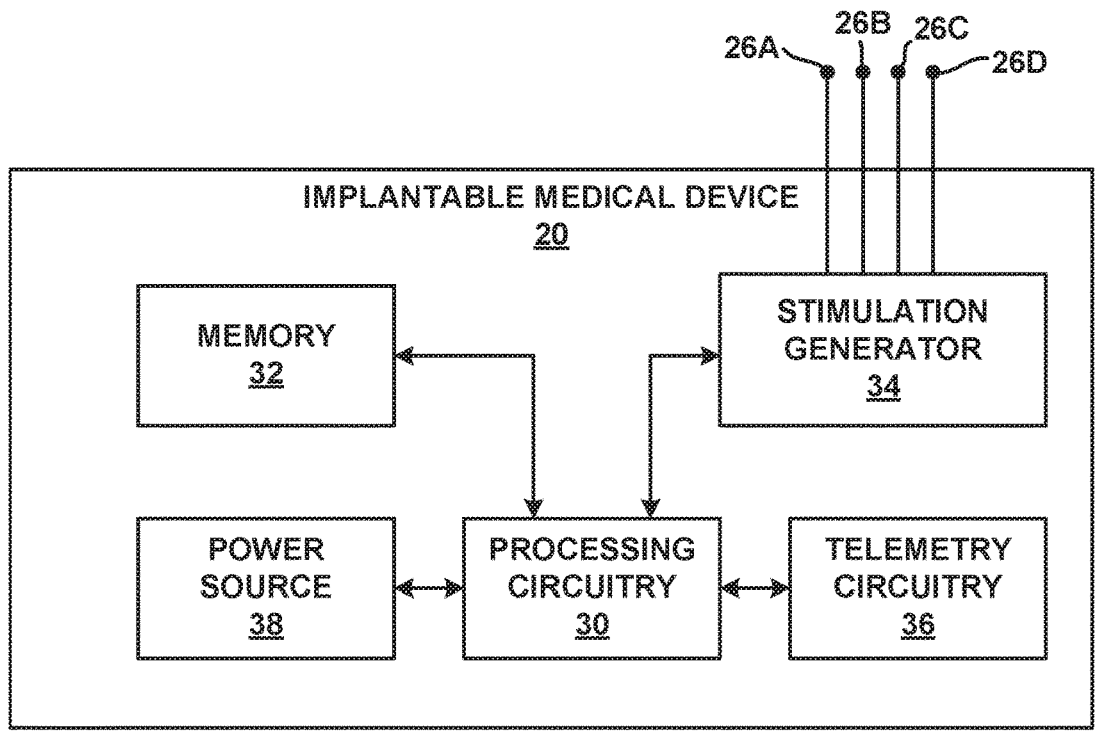
FIG. 3 is a functional block diagram of an example IMD configured to deliver stimulation therapy.

FIG. 3 is a functional block diagram illustrating various components of an example IMD 20. As shown in FIG. 3, IMD 20 includes processing circuitry 30, memory 32, stimulation generator 34, telemetry circuitry 36, power source 38 and other various hardware components providing functionality for operation of the device. For example, IMD 20 includes programmable processing circuitry 30 to be configured to operate according to executable instructions, typically stored in a computer-readable medium or memory 32 such as static, random-access memory (SRAM) device or Flash memory device. IMD 20 may include additional discrete digital logic or analog circuitry not shown in FIG. 3.

Stimulation generator 34 may connect to one or more medical leads 26A-26D. IMD 20 may utilize stimulation generator 34 connected to one or more medical leads 26A-26D to detect and recognize irregularities with the patient requiring treatment and/or therapy based on instructions from processing circuitry 30. In some examples, IMD 20 may utilize stimulation generator 34 connected to one or more medical leads 26A-26D to provide treatment and/or therapy based on instructions from processing circuitry 30.

Telemetry circuitry 36 may comprise any unit capable of facilitating wireless data transfer between IMD 20 and an external programmer 40, where external programmer 40 may comprise an external medical device, a programming device, a remote telemetry station, a physician-activated device, a patient-activated device, a display device or any other type of device capable of sending and receiving signals to and from IMD 20. Telemetry circuitry 36 and external programmer 40 are respectively coupled to one or more antennas for facilitating the wireless data transfer. Telemetry circuitry 36 may be configured to perform any type of wireless communication. For example, telemetry circuitry 36 may send and receive radio frequency (RF) signals, infrared (IR) frequency signals, or other electromagnetic signals. Any of a variety of modulation techniques may be used to modulate data on a respective electromagnetic carrier wave. Alternatively, telemetry circuitry 36 may use sound waves for communicating data or may use the patient's tissue as the transmission medium for communicating with a programmer positioned on the skin of a patient. In any event, telemetry circuitry 36 facilitates wireless data transfer between IMD 20 and external programmer 40.

Power source 38 may be a rechargeable battery, such as a lithium ion or nickel metal hydride battery. Other rechargeable or conventional batteries may also be used. In some examples, external programmer 40 may be configured to recharge IMD 20 in addition to programming IMD 20.

Figure 4:
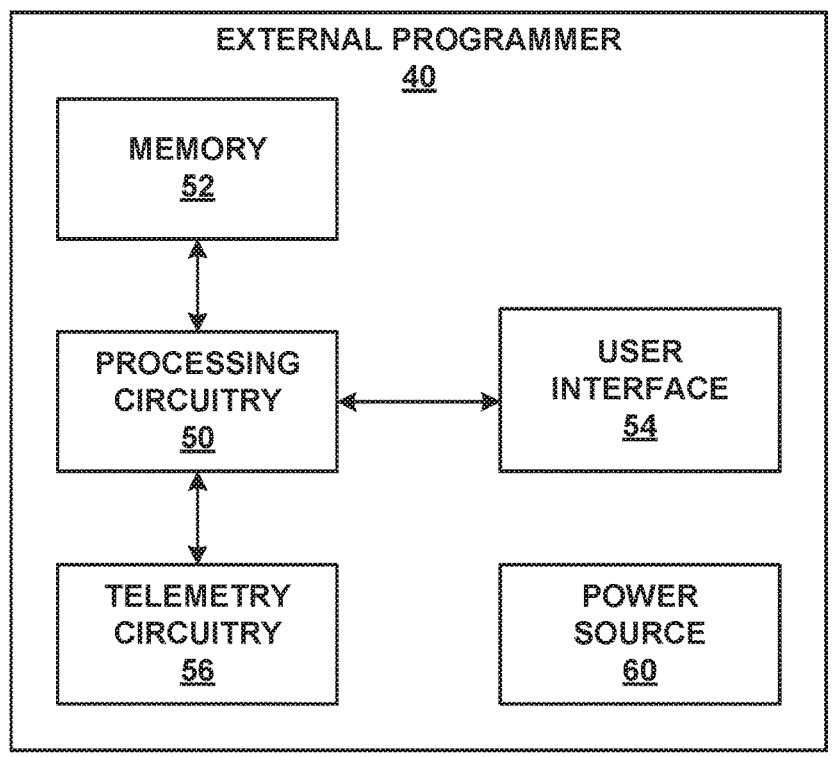
FIG. 4 is a functional block diagram of an example external programmer configured to communicate with the IMD of FIG. 3.

FIG. 4 is a functional block diagram illustrating various components of an external programmer 40 for use with IMD 20. As shown in FIG. 4, external programmer 40 includes user interface 54, processing circuitry 50, memory 52, telemetry circuitry 56, and power source 60. A clinician or patient interacts with user interface 54 in order to manually change the parameters of a therapy program, change therapy programs within a therapy of programs, view therapy information, view historical therapy regimens, establish new therapy regimens, or otherwise communicate with IMD, such as IMD 20 in FIG. 1, or view or edit programming information.

User interface 54 may include a screen and one or more input buttons, allowing external programmer 40 to receive input from a user. Alternatively, or additionally, user interface 54 may additionally, or only, utilize a touch screen display. The screen may be a liquid crystal display (LCD), dot matrix display, organic light-emitting diode (OLED) display, touch screen, or any other device capable of delivering and/or accepting information.

Figure 2:
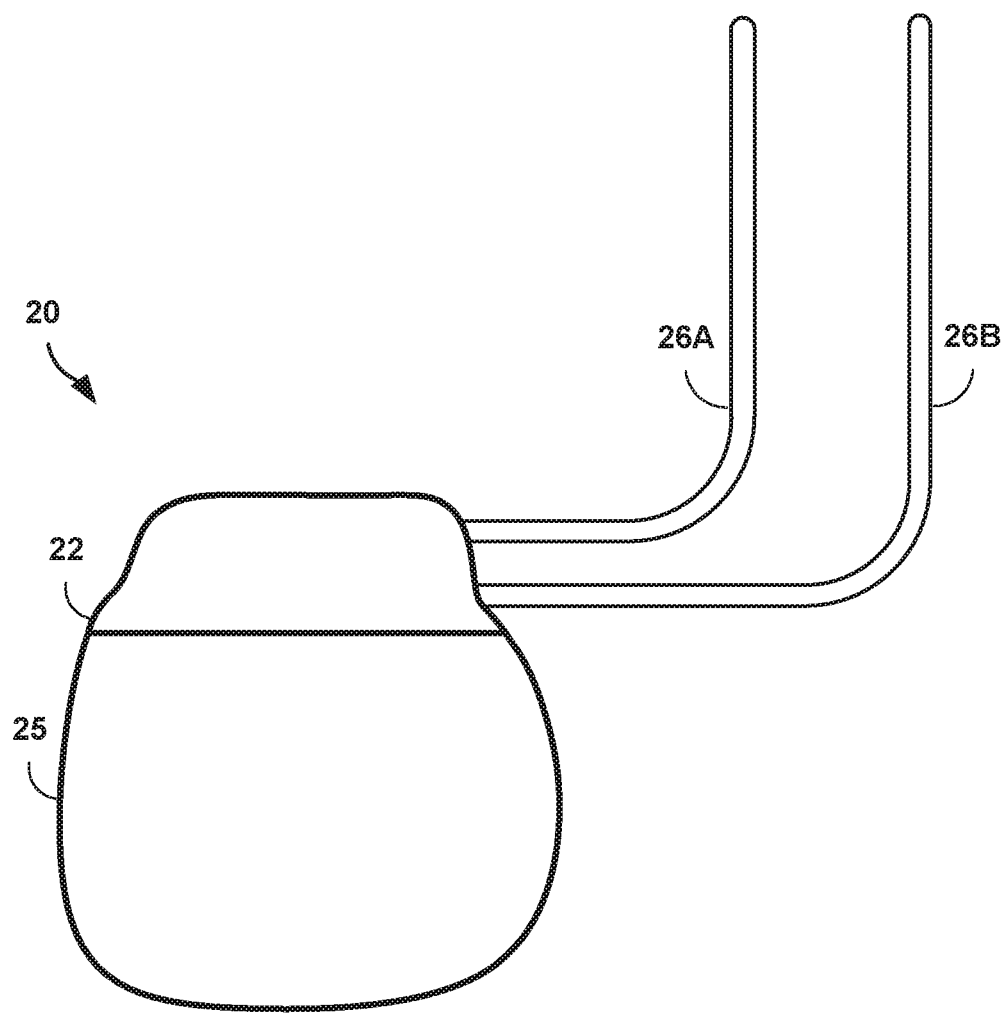
FIG. 2 is a conceptual diagram of an example IMD with a fastener device configured to secure a medical lead to the IMD.

Input buttons for user interface 54 may include a touch pad, increase and decrease buttons, emergency shut off button, and other buttons needed to control the therapy, as described above regarding patient programmer 40. Processing circuitry 50 controls user interface 54, retrieves data from memory 52 and stores data within memory 52. Processing circuitry 50 also controls the wireless transmission of data through telemetry circuitry 56 to an IMD, such as IMD 20 in FIGS. 1-2, by transmitting data to telemetry circuitry 36 as described in FIG. 3. The transmitted data may include therapy program information specifying various drug delivery program parameters. Memory 52 may include operational instructions for processing circuitry 50 and data related to therapy for the patient.

Power source 60 may be a rechargeable battery, such as a lithium ion or nickel metal hydride battery. Other rechargeable or conventional batteries may also be used. In some cases, external programmer 40 may be used when coupled to an alternating current (AC) outlet, i.e., AC line power, either directly or via an AC/DC adapter. In some examples, external programmer 40 may be configured to recharge IMD 20 in addition to programming IMD 20.

Figure 5:
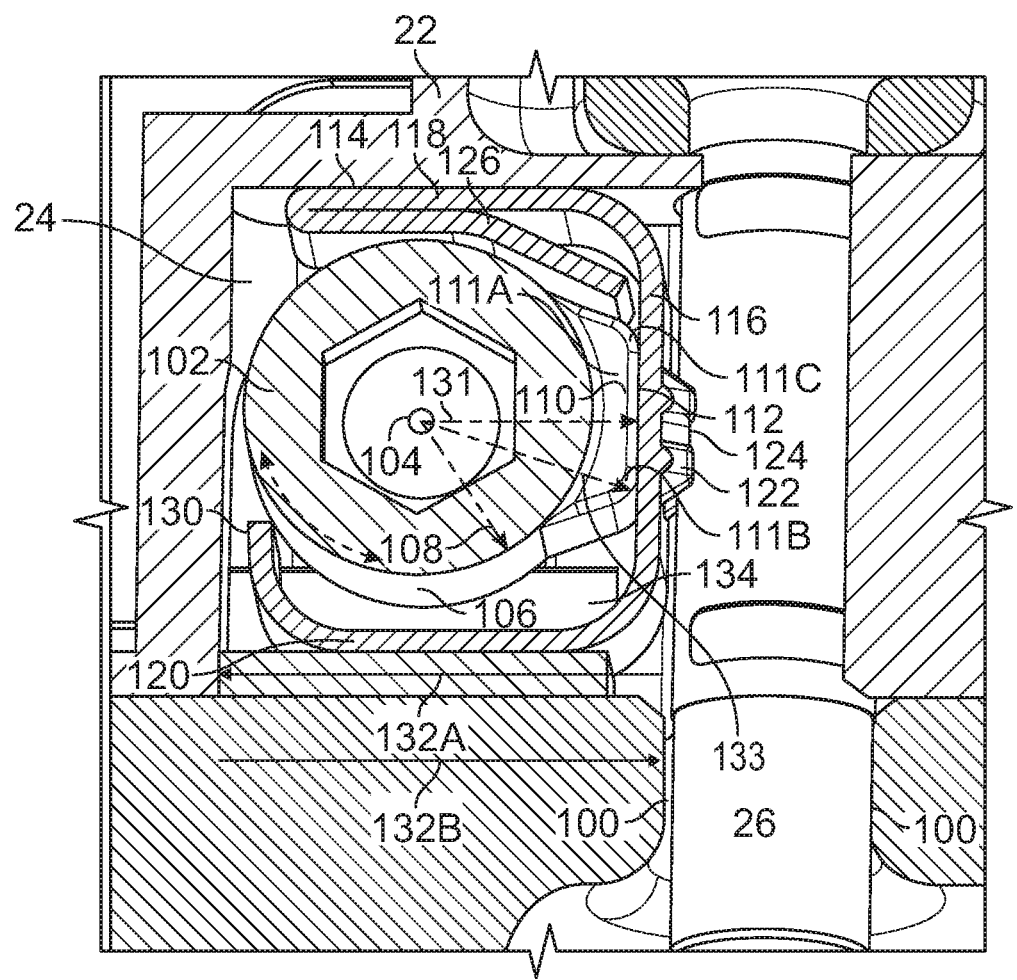
FIG. 5 is a conceptual diagram of an example fastener device, including a rotatable member with a cam lobe configured to actuate a slider.

FIG. 5 illustrates an elevated view of the components of fastener device 24 within a medical device 20 having a housing 25 which defines a channel 100 configured to receive an electrical lead 26 or leads 26A and 26B. A rotatable member 102 defines a longitudinal axis 104 about which the rotatable member 102 is configured to rotate in a clockwise and/or counterclockwise manner. The rotatable member 102 can be constructed out of metal alloys or polymers. Conductive materials can be utilized if rotatable member 102 is desired to be electrically conductive. The rotatable member 102 defines an outer surface 106 having a first radius 108 from the longitudinal axis 104. A cam lobe 110 extends out from the outer surface 106 farther from the longitudinal axis 104 than the first radius 108 of the outer surface 106. The cam lobe 110 defines a substantially planar surface 112 (also shown in FIG. 7) parallel to the longitudinal axis 104. The substantially planar surface 112 of the cam lobe 110 can be configured to retain the electrical lead 26 within the channel 100. As discussed above, the substantially planar surface can be flat, near flat or almost flat, but is not required to be absolutely flat.

Substantially planar surface 112 may define a midsection 111A between edges 111B and 111C. By being substantially planar, both of edges 111B and 111C have a larger radius 133 from longitudinal axis 104 than the radius 131 from longitudinal axis 104 to midsection 111A. From the Pythagorean theorem: $c=(a^2+b^2)^{1/2}$, we know if "a" (e.g., the radius 131) remains constant and "b" (e.g., the length of the substantially planar surface 112) increases, then "c" (the radius 133) will increase as well. More succinctly expressed, if "a" remains constant and "b" increases, then "c" will increase as well. Thus, in one example, if the flat surface 110 of the cam 131 is 0.0540 inches (1.3716 mm) and the substantially planar surface 112 is 0.0540 inches (1.397 mm), then radius 133 is 0.0590 inches (1.4986 mm). In this manner, a larger rotational force is needed to rotate rotatable member 102 and overcome the larger radius and force applied by either of edges 111B and 111C against the lead during rotation than the smaller radius 131 to midsection 111A will require. The dimensional difference between the radius 133 and the radius 131 is 0.059-0.054=0.005 inches (1.4986-1.3716=0.127 mm). The 0.005 inch (0.127 mm) is the amount of over-compression the lead has to temporarily endure for the cam lobe to rotate to the substantially planar surface. This configuration of midsection 111A between 111B and 111C may resist undesired rotation of rotatable member 102 when the lead is retained by cam lobe 110 of rotatable member 102. Further, to minimize the pressure applied to the lead when rotating the cam lobe 110 the curvature could be increased from zero, which would indicate a shape corner, to say R0.010 indicating a soft corner as shown by edges 111B and 111C in FIG. 5.

While the longitudinal axis 104 is shown as perpendicular to channel 100, the longitudinal axis 104 could also be parallel to or oblique to channel 100 so long as rotation of rotatable member 102 causes cam lobe 110 to extend into channel 100 and against electrical lead 26 within channel 100.

Further shown in FIG. 5, slider 114 defines a central portion 116 substantially parallel with the channel 100. Slider 114 may be made of a metal alloy if it is desirable for slider 114 to be conductive or from a polymer if it is desired for slider 114 to be non-conductive. Central portion 116 of slider 114 terminates into a first end 118 and a second end 120 which both extend away from the channel 100 and can be perpendicular to the longitudinal axis 104. In some examples, first end 118 and second end 120 extend in a direction substantially orthogonal from central portion 116. The slider 114 can be configured to slide into contact with the electrical lead 26 and secure the electrical lead 26 within the channel 100. When the rotatable member 102 is rotated (e.g., in a clockwise direction as shown in FIG. 5, (but a counter-clockwise direction may be used in other examples) cam lobe 110 engages the central portion 116 of the slider 114 to apply a force to the central portion 116 which pushes the slider 114 (to the right in FIG. 5) toward the channel 100. This action of a slider is discussed in greater detail below with reference to FIGS. 11A-I).

A slider protrusion 122 can be located on the central portion 116 of the slider 114 facing the channel 100. The slider protrusion 122 defines a substantially planar surface 124 parallel to the channel 100 and the cam lobe 110. The slider protrusion 122 can engage the electrical lead 26 as the rotatable member 102 is rotated toward the center portion 116.

A cam stop 126 can be operably coupled to the first end 118 and can extend inward toward the rotatable member 102 and can run along first end 118. The cam stop can be configured to contact and restrict rotation of the rotatable member 102 when the cam lobe 110 engages the cam stop 126 during rotation.

A retraction member 130 can be operably coupled to the second end 120 and extend toward the rotatable member 102 substantially parallel to the channel 100. The retraction member 130 is configured to contact the cam lobe 110 during rotation of the rotatable member 102 in a retraction direction (a counterclockwise direction as shown in FIG. 5). As the cam lobe 110 engages the retraction member 130, force from the cam lobe 110 pushes the slider 114 away from the channel along line of motion arrow 132A.

Slider 114, along with rotatable member 102, are housed within chamber 134. Slider 114 has a range of motion along motion arrow 132A and arrow 132B. As rotatable member 102 is configured to move in a clockwise or counterclockwise direction, cam lobe 110 will either engage center portion 116, cam stop 126 or retraction member 130 at respective circumferential positions of rotatable member 102. In response to cam lobe 110 engaging center portion 116, force from cam lobe 110 will cause slider 114 to slide toward the channel 100 along motion arrow 132B. When the cam lobe 110 contacts cam stop 126, cam stop 126 prevents rotatable member 102 from further rotation in the counterclockwise direction.

As shown in FIG. 5, when substantially planar portion 112 of cam lobe 110 is substantially parallel with slider center portion 126, this is a "locked position" and the force applied by cam lobe 110 to slider protrusion 122 to lead 26 will hold electrical lead 26 in place. As rotatable member 102 is rotated clockwise, cam lobe 110 disengages the center portion 116 and moves until it contacts retraction member 130. As cam lobe 110 presses against retraction member 130, slider 114 begins to slide away from channel 100 along motion arrow 132A until slider 114 is pushed away from channel 100. If a user keeps rotating rotatable member 102 past retraction member 130, cam lobe 110 will once again contact cam stop 126 which prevents further rotation. Although fastener device 24 may include slider 114, rotatable member 102 may function without slider 114 in other examples.

Figure 6A:
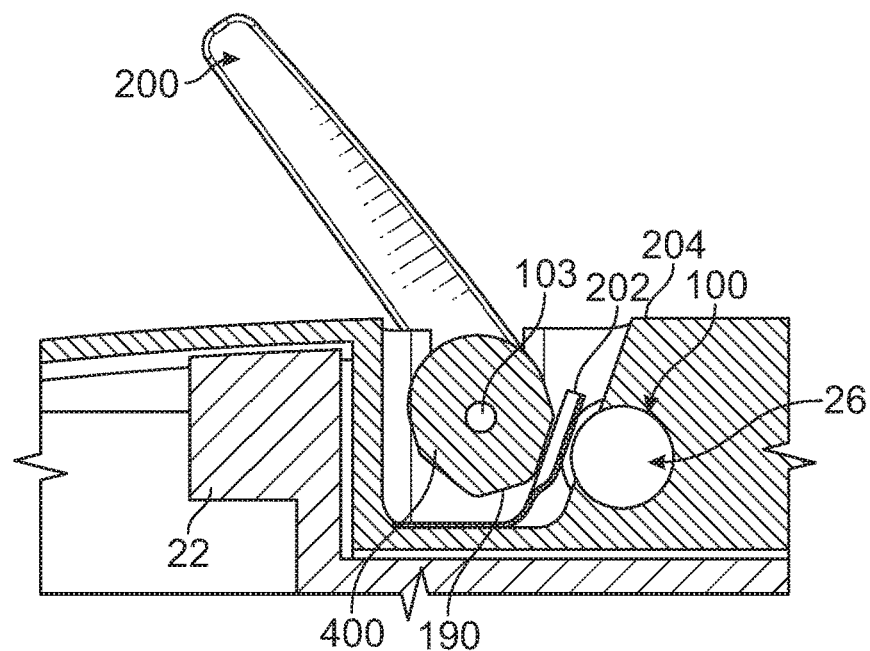
FIGS. 6A, 6B, and 6C are conceptual diagrams of an example rotatable member configured to actuate on a spring member.
Figure 6B:
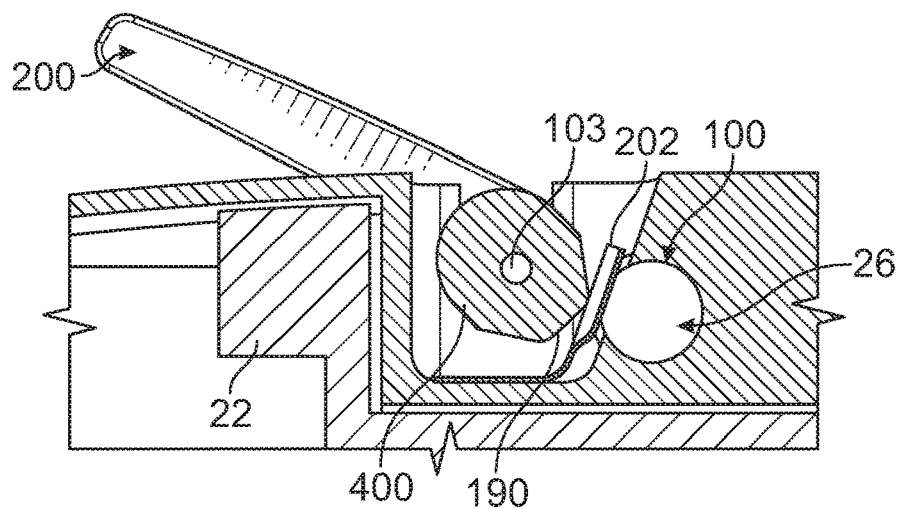
Figure 6C:
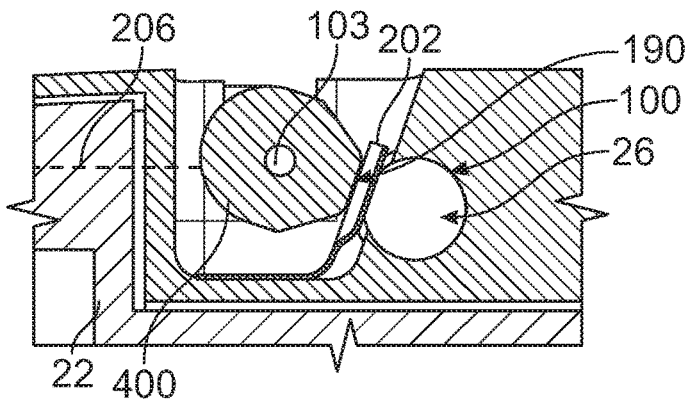

FIGS. 6A, 6B and 6C illustrate rotatable member 400. As shown, a lever 200 can extend from the rotatable member 400 perpendicular to the longitudinal axis 103. The lever 200 is configured to rotate the rotatable member 400 about the longitudinal axis 103. As shown in the example of FIG. 6A, an intermediary spring member 202 can be optional as a structure (like slider 114) positioned between the cam lobe 190 and electrical lead 26, when the cam lobe 190 is parallel to the channel 100. As shown in FIG. 6A, lever 200 is in an extended or released position in which a lead 26 can be inserted into, or removed from, channel 100. Like FIG. 5, when rotatable member 400 is turned clockwise by extending lever 200 in an upward fashion away from connector block 22, cam lobe 1+90 is positioned out and away from channel 100. Lever 200 is limited in rotation. Lever 200 can only move in an upward direction, or clockwise, until it hits edge 204 of connector block 22.

In operation, the user would move lever 200 upward as shown in FIG. 6A. An electrical lead 26 can be inserted into channel 100 in this configuration. After insertion of the electrical lead 26 into channel 100, the user could begin moving the lever 200 towards connector block 22 and thus begin to turn rotatable member 400 in a counterclockwise direction to rotate cam lobe 190 toward channel 100 as shown in FIG. 6B. In a locked position, as shown in FIG. 6C, lever 200 has been fully rotated to position cam lobe 190 as resting against spring 202 which in turn rests against the electrical lead 26 to hold lead 26 in place. It is noted spring 202 may not be used in other examples, so cam lobe 190 contacts the lead. As can be seen in FIG. 6C, lever 200 can rest in a lever channel 206 within connector block 22 to make lever 200 both flush with the connector block 22 and retain stop lever 200 at a position where the cam lobe 190 is in the locked position. The intermediary spring 202 can include a protrusion or structure configured to impinge or otherwise provide the forces of the cam lobe 190 onto the electrical lead 26. In this manner, spring 202 may prevent the sliding and/or rotation from cam lobe 112 from moving or abrading the electrical lead 26.

Figure 7:
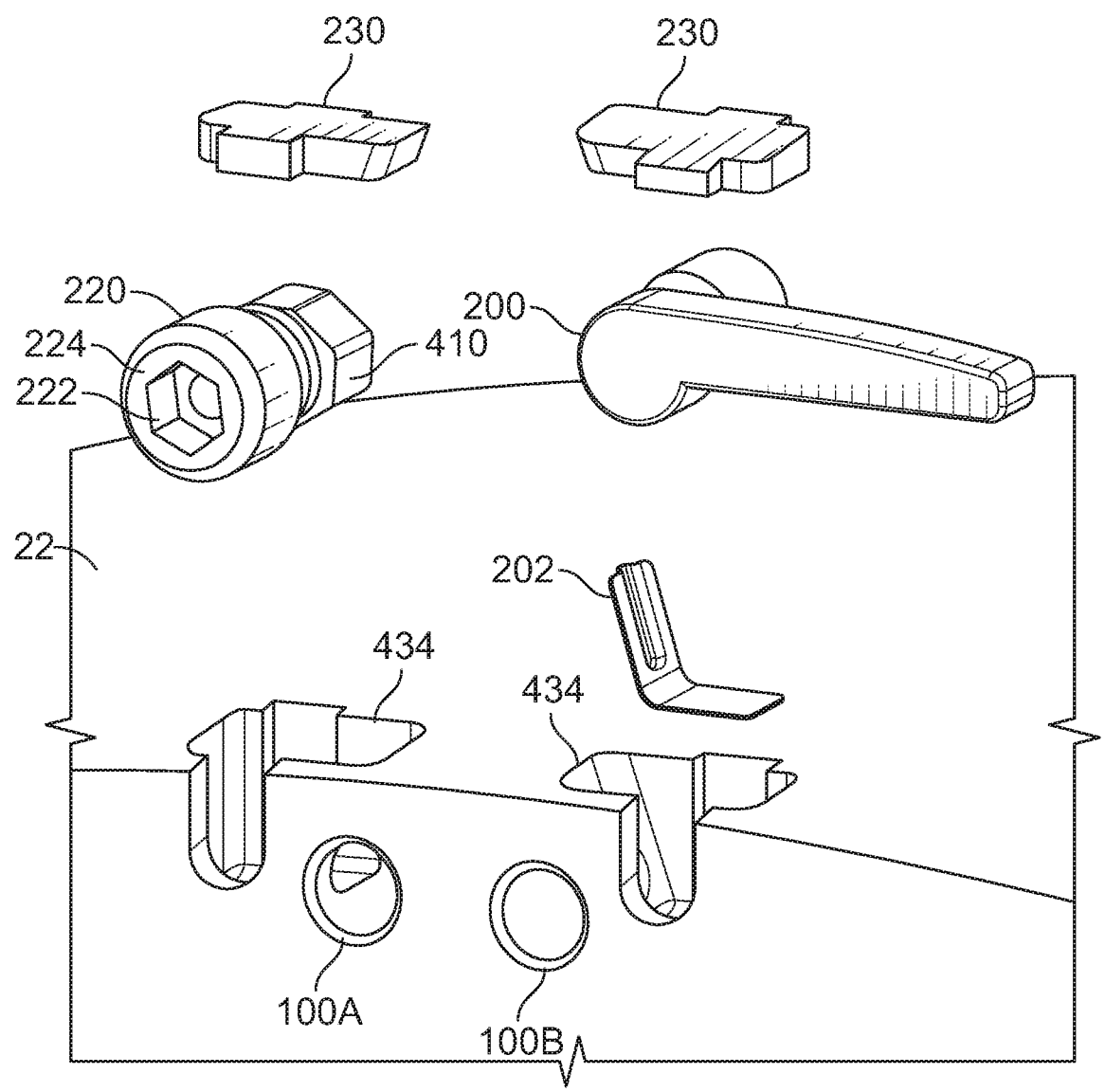
FIG. 7 is an exploded diagram of an example hex head rotatable member and an example lever rotatable member.

FIG. 7 illustrates an exploded view of examples of a hex head rotatable member 220 and a lever rotatable member 200 of FIGS. 6A-6C. Hex head rotatable member 220 may be like rotatable member 102 of FIG. 5. Lever 200 and intermediary spring 202 are shown in exploded view above a right chamber 434 and hex head rotatable member 220 is shown in exploded view above a left chamber 434. Chambers 434 are adjacent to respective channels 100A and 100B for electrical leads 26.

Hex head rotatable member 220 has a six-sided hexagonal indentation 222 defined in surface 224. Hexagonal indentation 222 is shaped to receive an Allen wrench. The Allen® wrench (or hex key) (not shown) is used by placing one end of an Allen wrench within the hexagonal indentation 222. The other end of the Allen® wrench (or hex key) is then held by a hand of a user to rotate rotatable member 220. Hex head rotatable member 200 is also shown having a cam lobe 410 which would also rotate as rotatable member 220 is rotated.

Both rotatable member 200 and 220 are placed within chambers 434 and flush mounted covers 230 are placed over chambers 434 to make connector block 22 flush on the surface and smooth for implantation. Covers 230 may be glued, welded, or otherwise fixed in place to connector block 22. Although connector block 22 is shown, rotatable members 200 and 220 may be placed directly within a housing of the medical device in other examples.

Figure 8A:
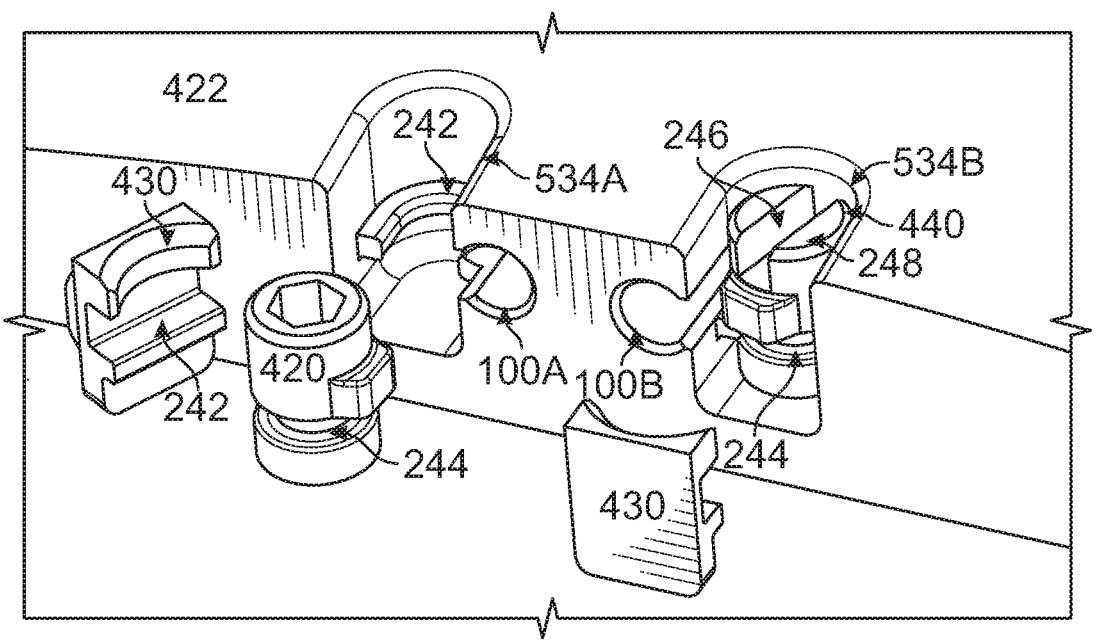
FIGS. 8A and 8B are conceptual diagrams of an example rotatable member configured to mechanically retain a medical lead to an IMD.
Figure 8B:
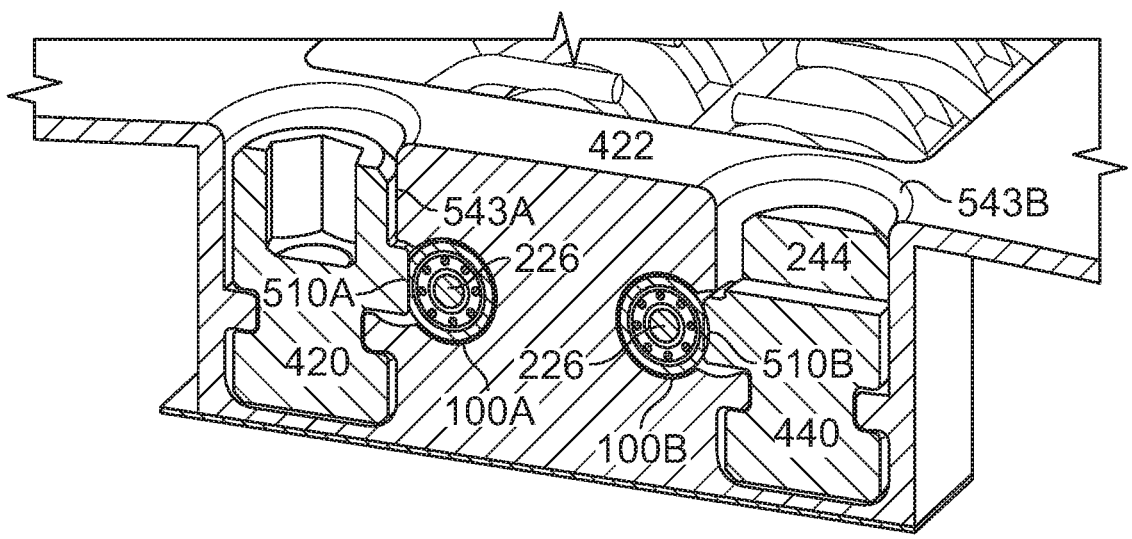

FIGS. 8A and 8B illustrate rotatable members 420 and 440 in a fully assembled configuration. As shown, hexagonal rotatable member 420 and slotted rotatable member 440 are shown being inserted into chambers 534A and 534B of connector block 422. With reference to FIG. 8A, hexagonal rotator member 420 and slotted member 440 are being inserted into chambers 534A and 534B respectively. It is of note, hexagonal rotator member 420 and slotted member 440 could be swapped into either chambers 534B and 534A as the same parts fit both chambers 534A and 534B. A ledge 242 (shown in chamber 534A) can traverse around a midsection surface of chambers 534A and 534B and at corresponding locations of respective covers 430. The ledge 242 can engage rotatable member slot 246 and provide support to hold rotatable member 420 and 440 securely within chambers 534A and 534B. Ledge 242 assures rotatable members 420 and 440 are held within chambers 534A and 534B. Ledge 242 rests within channel 244, which retains rotatable member 420 and 440 within chambers 534A and 534B respectively. Ledge 241 allows rotatable member 420 and 440 to also rotate freely within chamber 534A and 534B respectively while also retaining rotatable member 420 and 440 within chambers 534A and 524B. This ensures rotatable members cannot become lose within chambers 534A and/or 534B and possibly become lost or disassociated from IMD 20.

Slotted rotatable member 440 defines a slot 246 bisecting surface 248. Slot 246 is configured to receive a standard screwdriver which can rotate slotted rotatable member 440. The standard screwdriver can be used similarly to an Allen® wrench (or hex key) to rotate the rotatable member 440. It is of note, both rotatable member 420 and rotatable member 440 could be a hex head rotatable member like rotatable member 420 or both could be a slotted rotatable member like rotatable member 440.

With reference to FIG. 8B, a cross-section of the connector block 422 is shown with hexagonal rotatable member 420 and slotted rotatable member 440 installed. As shown both rotatable members 420 and 440 have their cam lobes 510A and 510B respectively in a "locked position" where electrical leads 226A and 226B are held in frictional position by the cam lobes 510A and 510B. It's of note neither rotatable member 420 nor 440 utilizes an intermediary spring 202. Further, almost any type of standardized aperture for use with a Phillips® screwdriver, an Allen® wrench (or hex key), torx wrench, a bristol wrench, or any other shape to facilitate rotation of rotatable member 420, 440 or 102 can be used with a standard or proprietary tool.

Figure 8C:
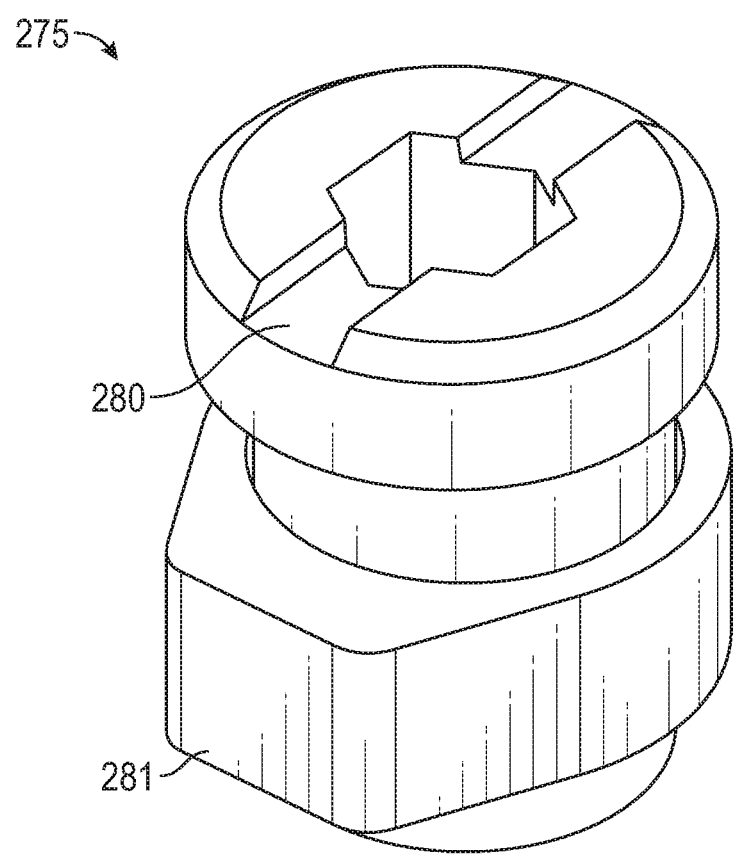
FIG. 8C is a conceptual diagram of an example hexagonal rotatable member configured to mechanically retain a medical lead to an IMD.

With reference to FIG. 8C, a slotted hexagonal rotatable member 27S is shown. As shown rotatable members 27S has cam lobe 281 and hex-slotted recess 280. Rotatable member 27S could be used with most any type of implant tool, such as a standard screwdriver or an Allen® wrench (or hex key). The hex-slotted recess 280 allows for an implanting physician to utilize either a standard screwdriver or an Allen wrench for coupling of the electrical lead to the IMD.

Figure 9A:
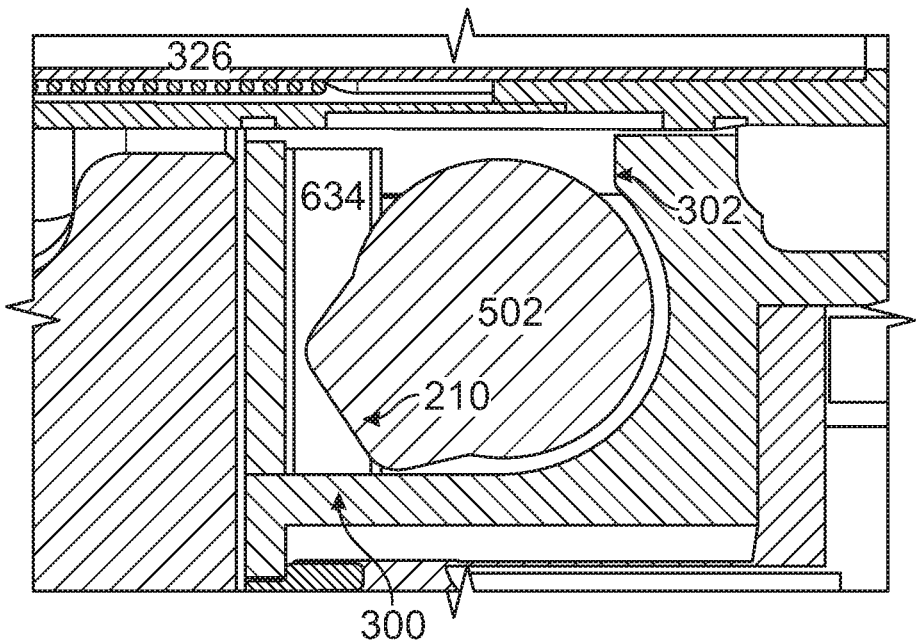
FIGS. 9A and 9B are a conceptual diagram of an example rotatable member within a chamber defining hard stops.
Figure 9B:
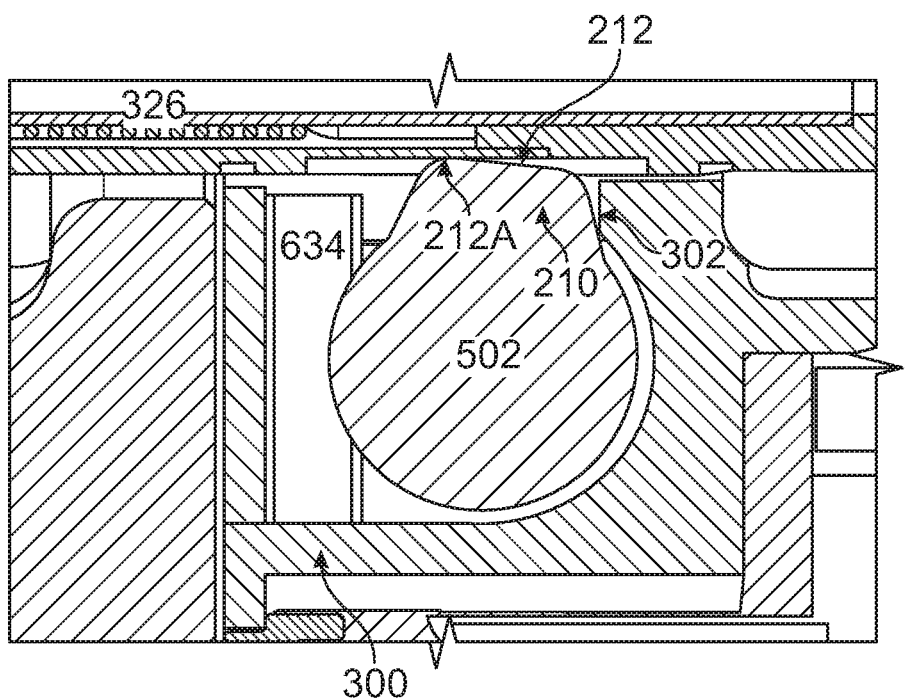

FIGS. 9A and 9B are a conceptual diagram of a rotating member 502 within a chamber 634 which provides hard stops to prevent rotation of rotating member 502 beyond certain circumferential positions for the rotating member 502. Chamber 634 can provide built in hard stops for rotating member 502. Hard stops can assist an implantation physician with determining when the rotating member 502 is in the "locked position" and the "unlocked position." Without hard stops 300 and 302, rotating member 502 would continue to rotate in response to rotational force from the implantation physician. Thus, the physician may have difficulty identifying the fully "locked position" or an "unlocked position" by feel alone. Therefore, hard stops 300 and 302 may facilitate correct positioning of the rotatable member with respect to the lead 326.

When rotatable member 502 is rotated in a clockwise direction, cam lobe 210 will eventually contact hard stop 302, as shown in FIG. 9B, and stop rotating. In this position, rotatable member is in a substantially "locked position" at which cam lobe 210 has engaged electrical lead 326 within channel 100. The implanting physician could simply turn the rotatable member 502 counterclockwise a short distance to fully engage the substantially planar surface 212 against electrical lead 326 thus providing a more secure electrical lead retaining position. The implanting physician should be able to feel the rotating member 502 substantially planar surface 212 engaging electrical lead 326 and being slightly harder to turn in a counterclockwise motion as the electrical lead 2626 would provide resistance force to the rotating movement. The hard stop 302 could be set so the cam lobe 210 is in the "locked position" when the cam lobe 210 is engaged with hard stop 302. Another alternative is to provide for the forces against cam lobe edge 212A of planar surface 212 to cause the cam lobe 210 to settle with the planar surface 212 against the lead 326.

If the implanting physician needs to release the electrical lead 326 from channel 100, the implanting physician would turn the rotatable member 502 in a counterclockwise direction. The implanting physician could rotate the rotatable member 502 until the cam lobe 210 engaged hard stop 300 indicating the rotatable member 502 is in an "unlocked position" at which the lead 326 may be removed from the channel 100.

Figure 10A:
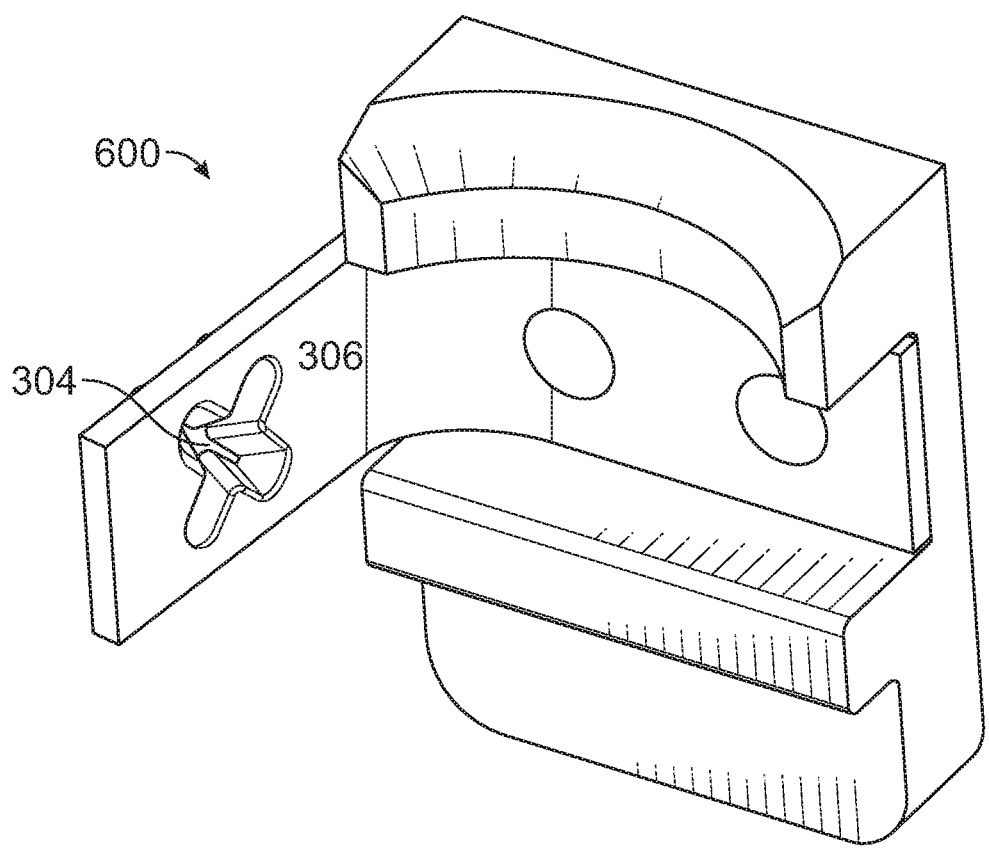
FIGS. 10A and 10B are conceptual diagrams of an example intermediary impinger configured to mechanically hold a medical lead within an IMD.
Figure 10B:
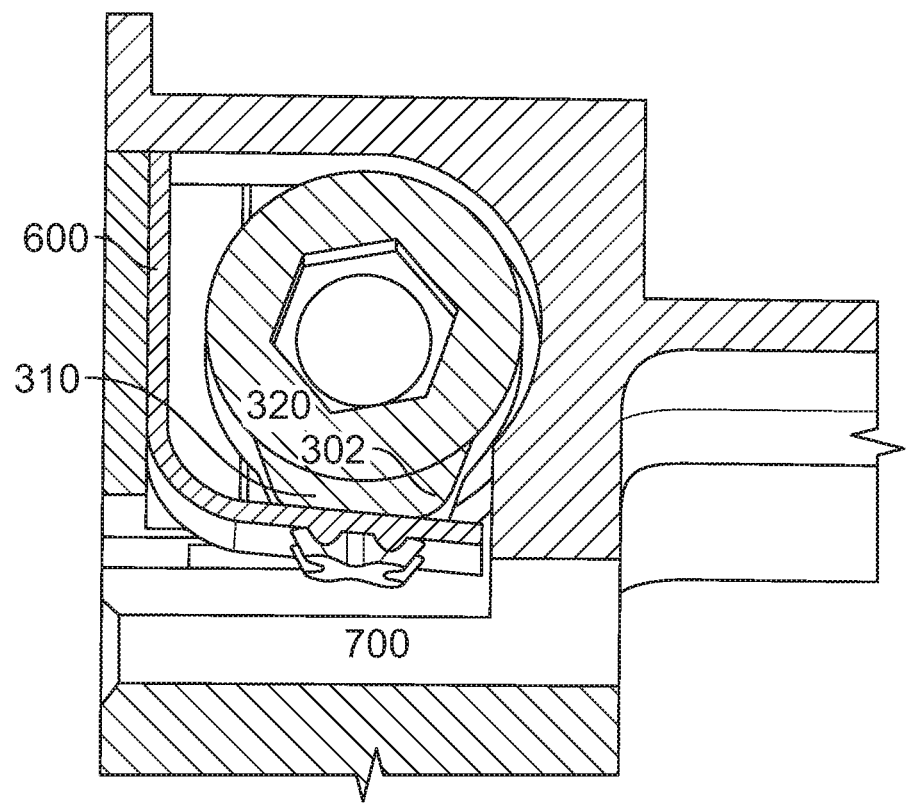

FIGS. 10A and 10B are conceptual diagrams illustrating an example of an intermediary impinger 600 configured to mechanically connect a medical lead to an IMD. Intermediary impinger 600 can behave like spring 202 of FIGS. 6A-6C. Intermediary impinger 600 can function to convert the rotational motion of rotational member 320 into linear movement from cam lobe 310 forces against intermediary impinger 600 to electrical lead 26 within channel 700. Utilizing an intermediary impinger 600 can reduce or prevent movement of the electrical lead 26 from causing rotation of the rotatable member 320. As an example, if the lead 26 moves for whatever reason (e.g., patient movement), impinger 600 prevents this movement from being transferred to rotatable member 320, as impinger 600 cannot move in a direction parallel with the channel 700. If the impinger 700 were not present, the parallel force could pull the cam lobe 310 and cause rotation of rotatable member 320 until the cam lobe 310 no longer locked the lead 26 in place.

In another variation of spring 202, intermediary impinger 700 has an "X"-shaped protrusion 304, which when cam lobe 310 engages contact surface 306, protrusion 304 extends toward channel 700 and engages electrical lead 26. Protrusion 304 may be configured to have any type of structure or include a plurality of discontinuous projections.

FIGS. 11A-I illustrate a process of insertion and retention of an electrical lead within an IMD utilizing a slider and rotatable member. Electrical lead 426 is shown being inserted within channel 800 in the example FIG. 11A (see state 1000 FIG. 12).

Figure 11A:
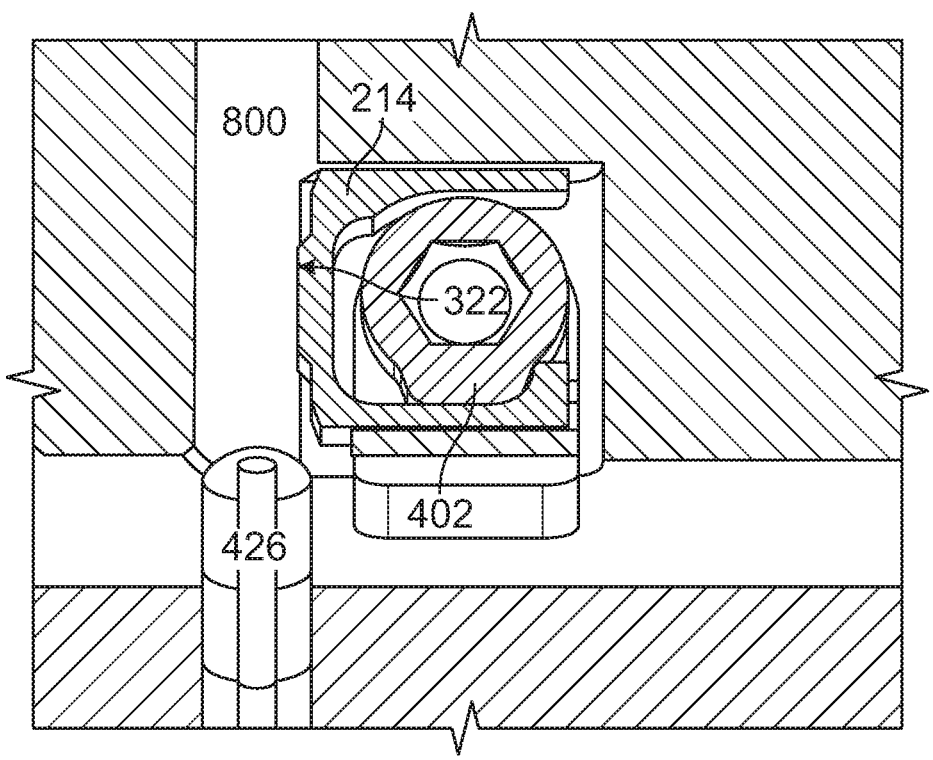
Figure 11B:
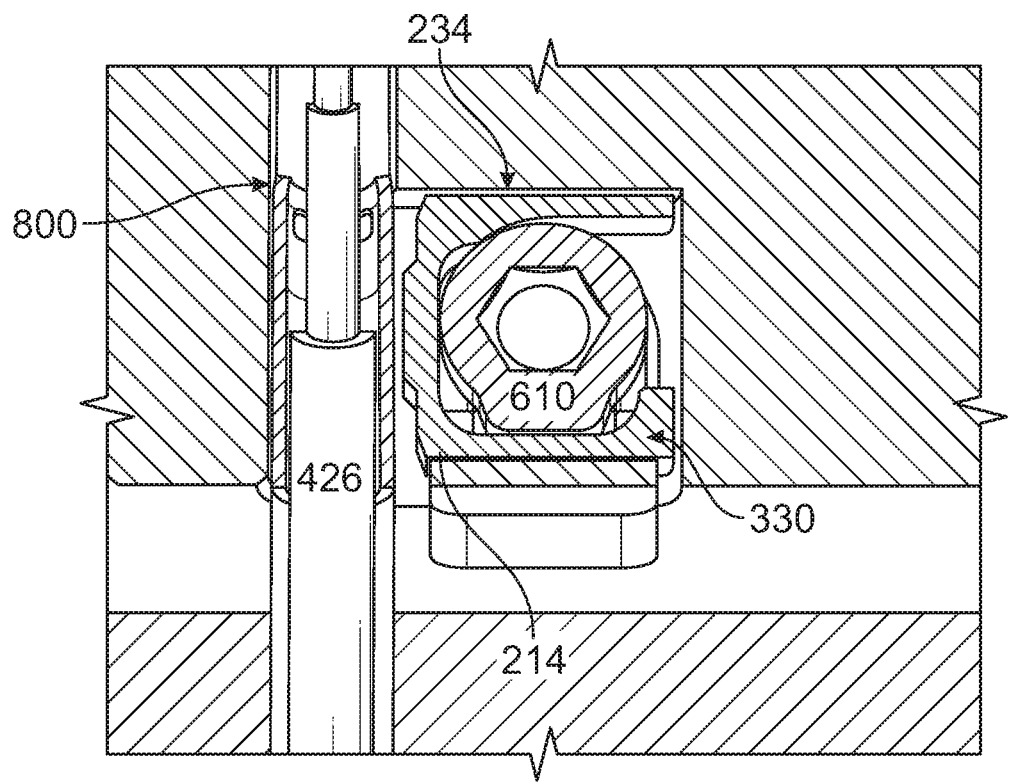
Figure 11C:
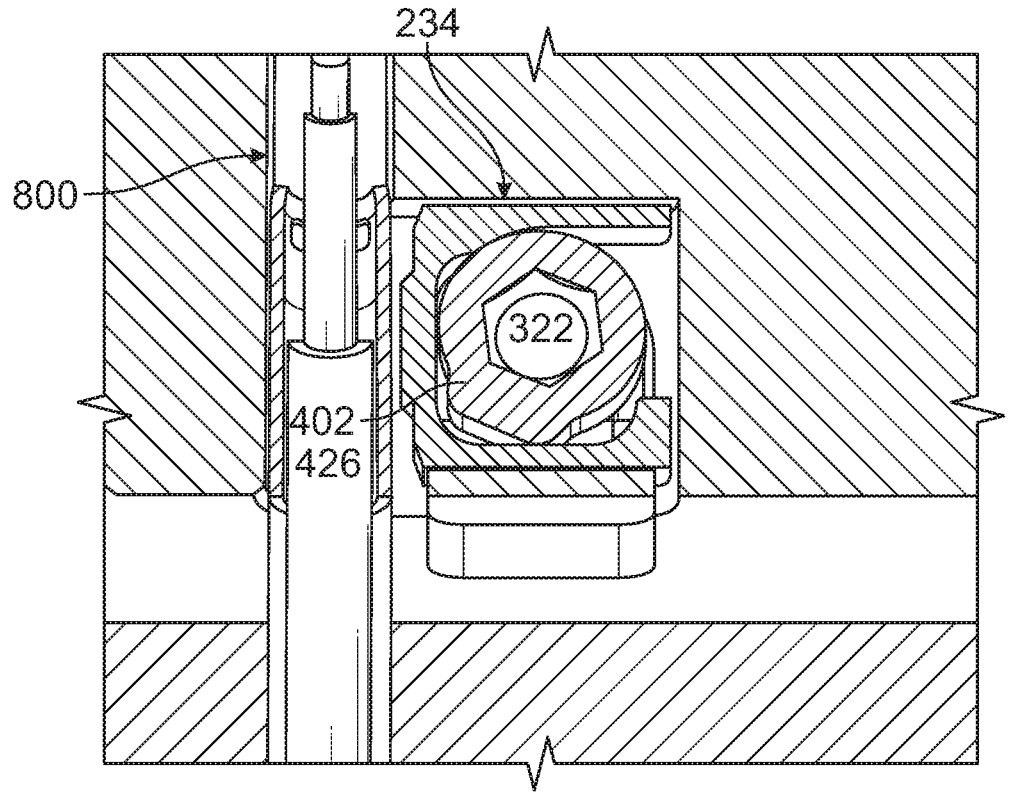

With reference to FIG. 11B, lead 426 is fully inserted within channel 800. With reference to FIG. 11C in which the lead is fully inserted into channel 800, an implanting physician can engage an Allen® wrench (or hex key) in hexagonal indentation 322 and begin turning hex head rotatable member 402 clockwise (see state 1002 FIG. 12). Rotation of rotatable member 402 causes cam lobe 610 to contact and push slider 214 towards the lead 426 in channel 800 in. Slider 214 moves toward lead 436 in chamber 234, which is shown by cam lobe 610 moving away from retraction member 330.

Figure 11D:
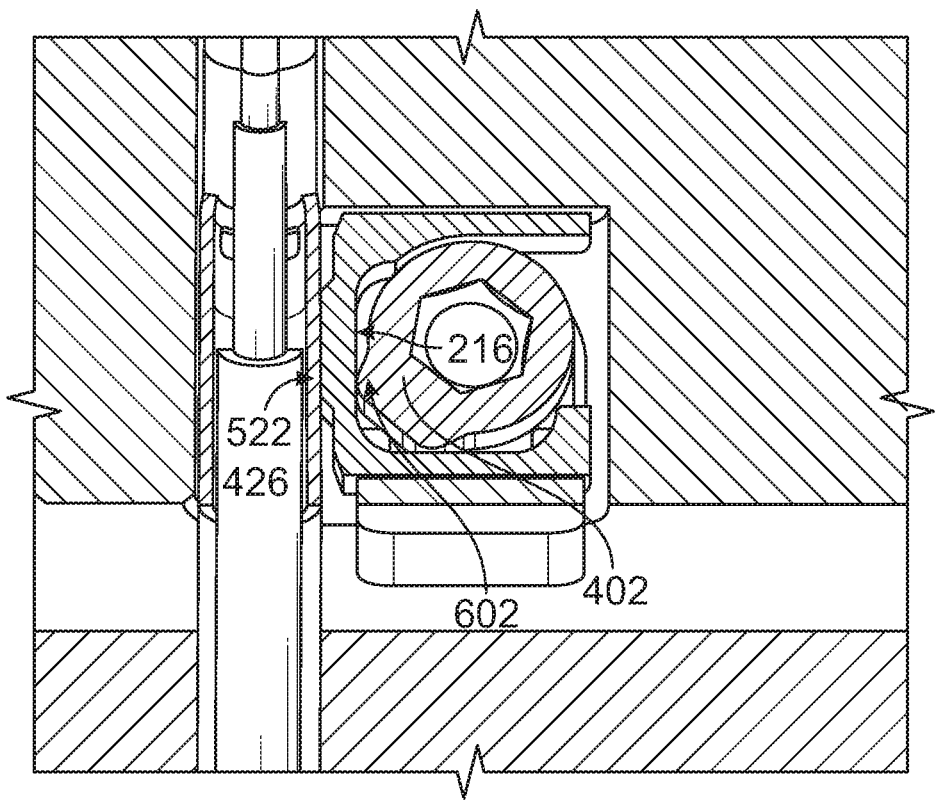
Figure 11E:
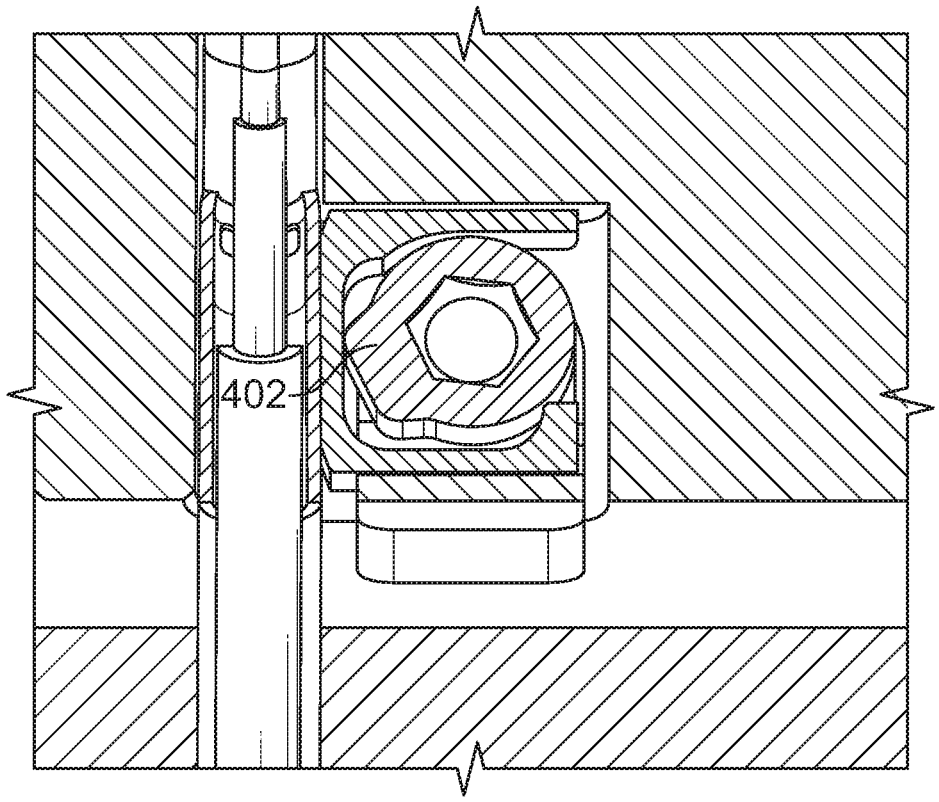
Figure 12:
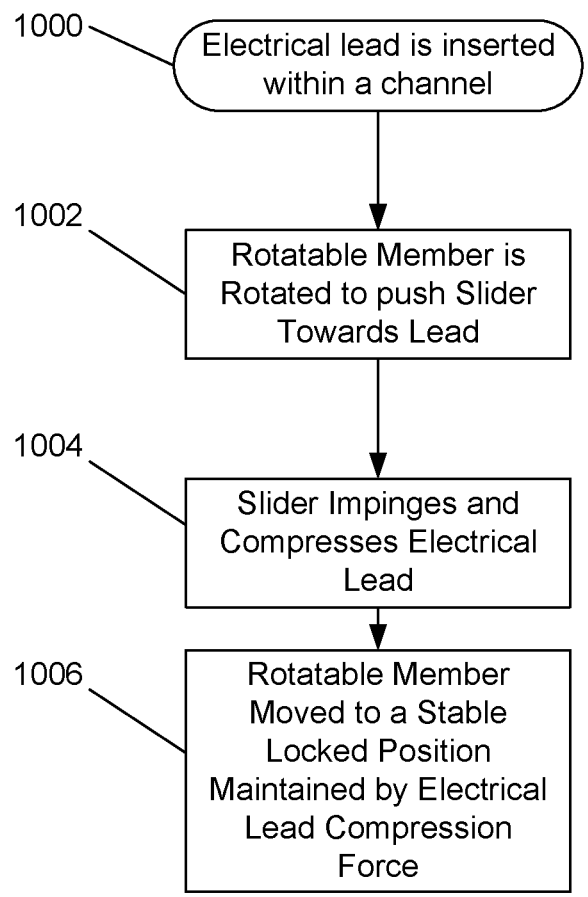
FIG. 12 is a flowchart diagram of a process for inserting and securing a lead.

With reference to FIGS. 11D and 11E, hex head rotatable member 402 continues to move in a clockwise direction and now cam lobe corner 602 engages slider center portion 216 and applies a force to slider 214 in the direction of channel 800 to push slider 214 towards channel 800 and the lead 426 so slider protrusion 522 begins to engage the electrical lead 426 (see state 1004 at FIG. 12).

Figure 11F:
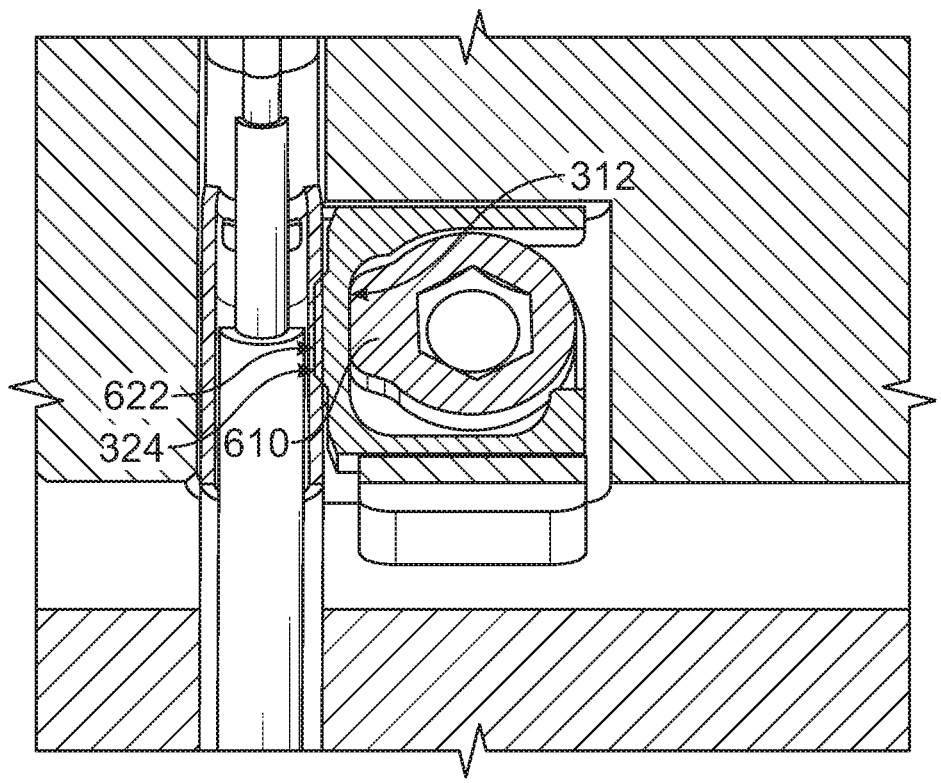
Figure 11G:
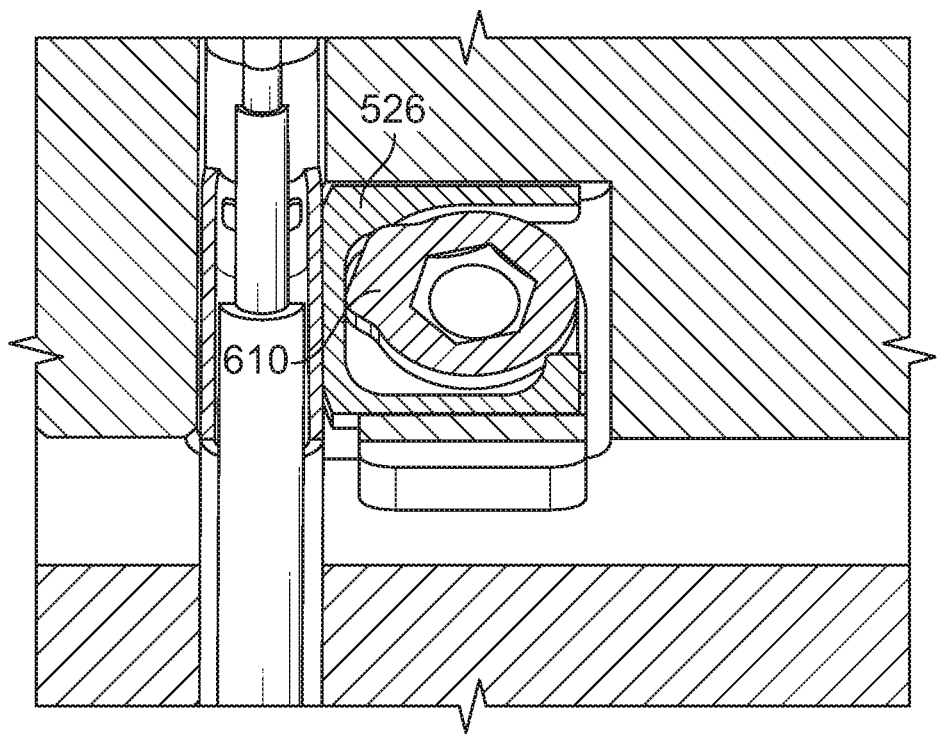

With reference to FIGS. 11F and 11G, hex head rotatable member 402 continues to move in a clockwise direction and in FIG. 11F is in a "locked position", where the substantially planar surface 312 of cam lobe 610 is substantially parallel with the substantially planar surface 324 of slider protrusion 622 (see state 1006 FIG. 12). With reference to FIG. 11G, if the implanting physician keeps rotating the hex head rotatable member 402 past the "locked position," cam lobe 610 will engage cam stop 526. Slider 214 is still holding the electrical lead 426 even though the implanting physician has rotated past the "locked position." The lead 426 will likely push back against the slider 214, which would center the cam lobe 610 again on the slider 214 to the equilibrium of the "locked position" of FIG. 11F which has a predetermined amount of force and pressure against the lead 426 for retention.

Figure 11H:
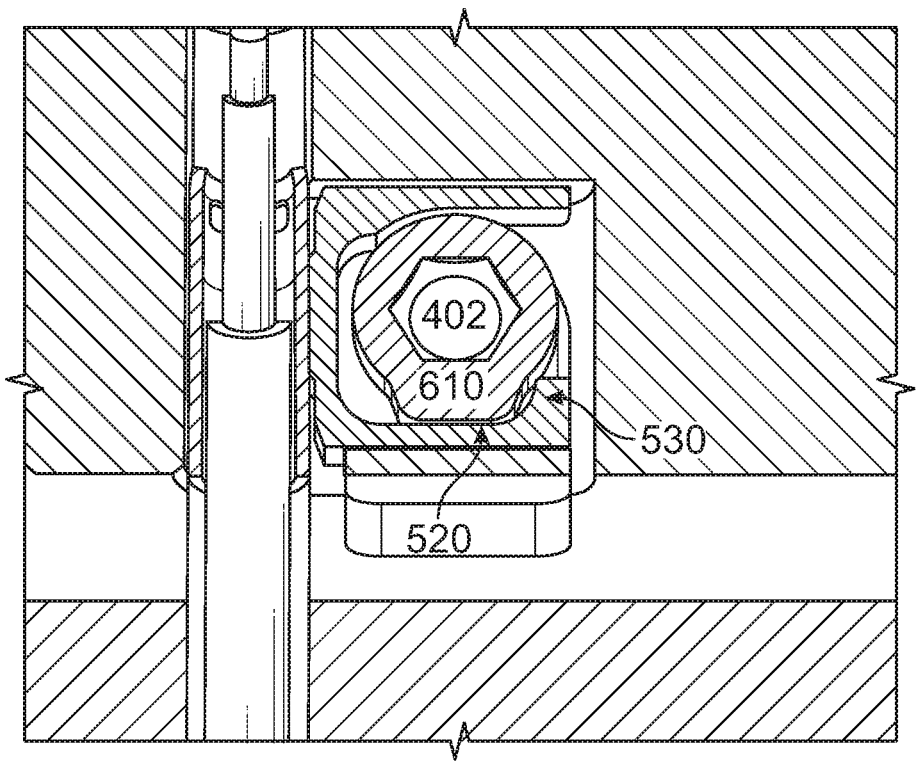
Figure 11I:
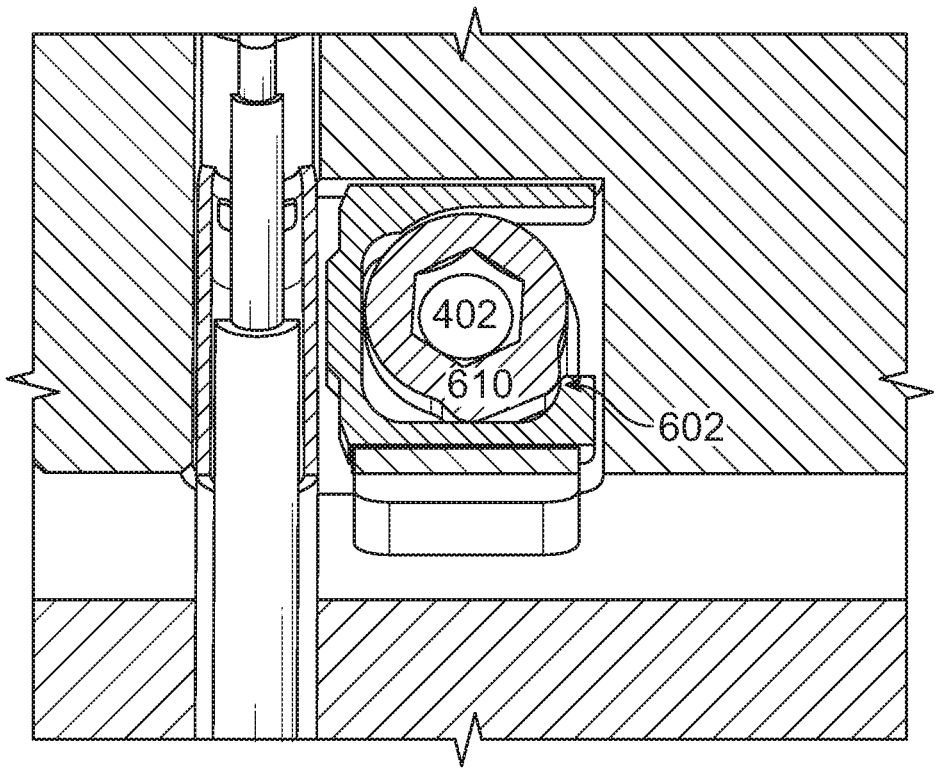
Figure 11J:
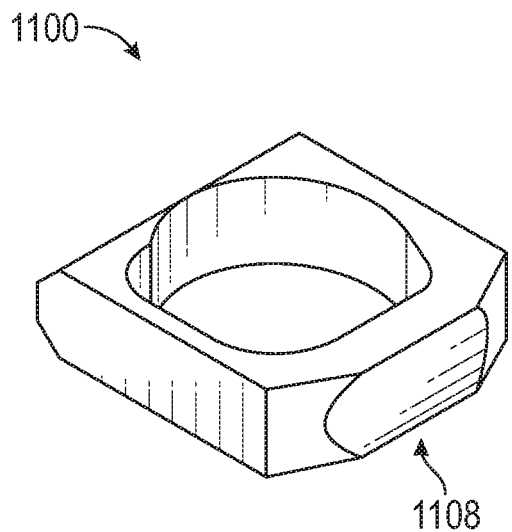
FIGS. 11J, 11K, 11L and 11M are conceptual diagrams illustrating an example slider device for securing a medical lead to an IMD with a rotatable member.
Figure 11K:
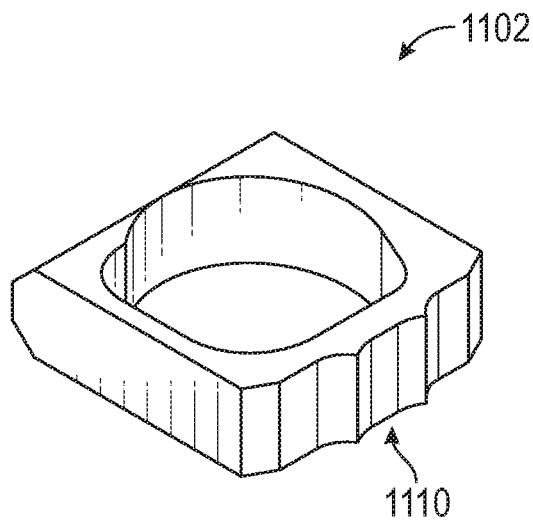
Figure 11L:
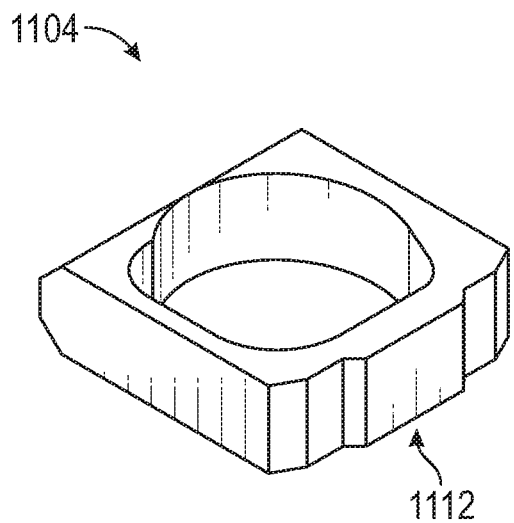
Figure 11M:
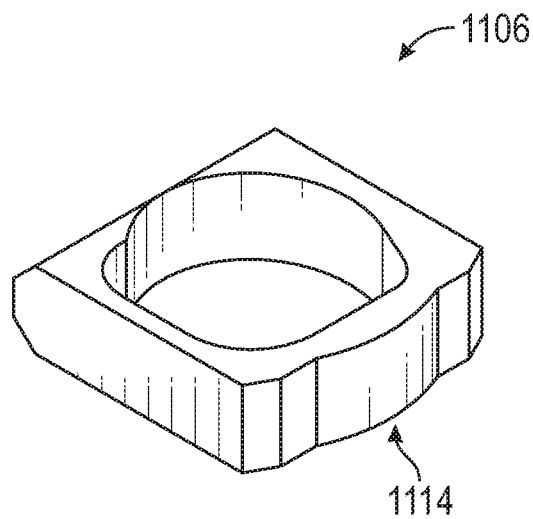
Figure 13:
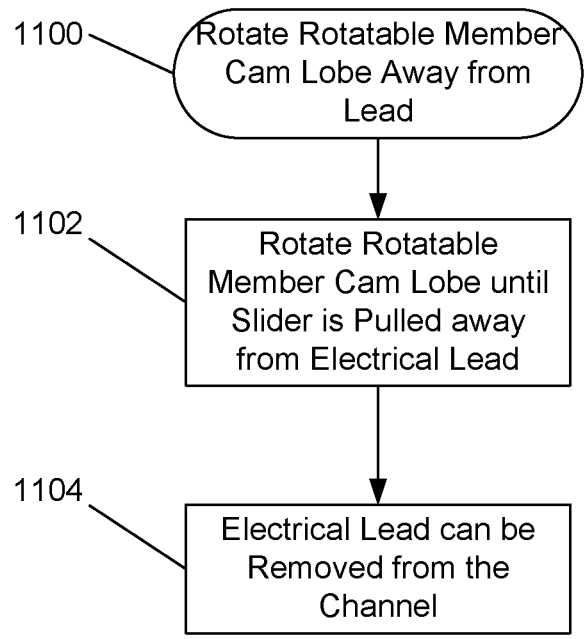
FIG. 13 is a flowchart diagram of a process for removing a lead.

In some examples, a lead may need to be removed from a medical device. As shown in FIGS. 11H and 11I, the implanting physician may release the electrical lead 426 from channel 800 by using an Allen® wrench (or hex key) again to rotate hex head rotatable member 402 in a counterclockwise direction. As shown in FIG. 11H, cam lobe 610 is rotated away from lead 426 and is now facing slider second end 520 (see state 1100 in FIG. 13). In FIG. 11I, as the implanting physician keeps rotating hex head rotatable member 402, cam lobe corner 602 engages retraction member 530. As the implanting physician keeps rotating the rotatable member 402, cam lobe corner 602 pushes against the retraction member 530 to slide the slider 214 in a direction away from channel 800 and electrical lead 426 (see state 1102 in FIG. 13). Therefore, pulling slider 214 away from the lead 426 may overcome tissue ingress or other frictional forces otherwise holding the electrical lead 426 within the channel 800. Once the slider 214 is pulled away from electrical lead 426, then the implanting physician can remove electrical lead 426 from channel 800 (see state 1104 of FIG. 13).

FIGS. 11J, 11K, 11L and 11M are conceptual diagrams illustrating an example slider device for securing a medical lead to an IMD with a rotatable member. Sliders 1100, 1102, 1104 and 1106 all represent various examples of sliders which could be used to retain an implantable lead within a medical device in use with a rotatable member. Each of the slider protrusions for each of sliders 1100, 1102, 1104 and 1106 all provide unique differences all depending on the desired hold on the implantable lead or for the application the implantable lead is being used.

Slider protrusion 1108 shows an elongated concave structure. Slider protrusion 1108 allows the slider 1100 to better accept the implantable lead as the elongated concave structure is almost the same shape as out outer shell of an implantable lead. Thus, less force to placed upon an implantable lead and less risk of deformation of the implantable lead is realized as there are no pointed protruding surfaces in contact with the implantable lead.

Slide protrusion 1110 shows a dual ripple structure. Slider 1102 can localize the force applied to an implantable lead to two spots. Thus, the force exerted on the implantable lead would be localized to two spots. This is a variation on slide protrusions 1112 and 1114 which provide a distribution of the forces along the protrusions 1112 and 1114. For example, slider protrusion 1114 has a rounded edge and thus the force would be distributed along the slider protrusion with most of the force coming from the largest extending radius, which is in the middle of the slider protrusion. For the slider protrusion 1112, the protrusion 1112 is substantially flat, as discussed above, so the force is distributed equally along protrusion 1112.

The techniques described in this disclosure may be implemented, at least in part, in hardware, software, firmware or any combination thereof. For example, various aspects of the described techniques may be implemented within one or more processors or processing circuitry, including one or more microprocessors, digital signal processors (DSPs), application specific integrated circuits (ASICs), field programmable gate arrays (FPGAs), or any other equivalent integrated or discrete logic circuitry, as well as any combinations of such components. The term "processing circuitry" or "processing circuitry" may generally refer to any of the foregoing logic circuitry, alone or in combination with other logic circuitry, or any other equivalent circuitry. A control unit including hardware may also perform one or more of the techniques of this disclosure.

Such hardware, software, and firmware may be implemented within the same device or within separate devices to support the various operations and functions described in this disclosure. In addition, any of the described units, circuits or components may be implemented together or separately as discrete but interoperable logic devices. Depiction of different features as circuits or units is intended to highlight different functional aspects and does not necessarily imply such circuits or units must be realized by separate hardware or software components. Rather, functionality associated with one or more circuits or units may be performed by separate hardware or software components or integrated within common or separate hardware or software components.

The techniques described in this disclosure may also be embodied or encoded in a computer-readable medium, such as a computer-readable storage medium, containing instructions described as non-transitory media. Instructions embedded or encoded in a computer-readable storage medium may cause a programmable processing circuitry, or other processing circuitry, to perform the method, e.g., when the instructions are executed. Computer readable storage media may include random access memory (RAM), read only memory (ROM), programmable read only memory (PROM), erasable programmable read only memory (EPROM), electronically erasable programmable read only memory (EEPROM), flash memory, a hard disk, a CD-ROM, a floppy disk, a cassette, magnetic media, optical media, or other computer readable media.

Various examples of this disclosure have been described. These and other examples are within the scope of the following claims.

What is claimed is:

1. A medical device comprising:
   a housing defining a channel configured to receive an electrical lead; and
   a rotatable member defining a longitudinal axis about which the rotatable member is configured to rotate, wherein the rotatable member defines:
      an outer surface having a first radius from the longitudinal axis; and
      a cam lobe extending farther from the longitudinal axis than the first radius of the outer surface, the cam lobe defining a cam lobe surface parallel to the longitudinal axis, wherein the cam lobe surface defines a first portion at a first radius from the longitudinal axis, a second portion at a second radius from the longitudinal axis, and a midsection at a midsection radius from the longitudinal axis and between the first portion and the second portion, wherein the first radius and the second radius are larger than the midsection radius, and wherein the cam lobe surface of the cam lobe is configured to retain the electrical lead within the channel.

2. The medical device of claim 1, further comprising a lever extending from the rotatable member perpendicular to the longitudinal axis.

3. The medical device of claim 2, wherein the lever is configured to rotate the rotatable member about the longitudinal axis.

4. The medical device of claim 1, wherein the longitudinal axis is parallel to the channel receiving the electrical lead.

5. The medical device of claim 1, wherein the longitudinal axis is perpendicular to the channel receiving the electrical lead.

6. The medical device of claim 1, further comprising a slider having a central portion parallel with the cam lobe, the central portion terminating in a first end and a second end where both the first end and the second end extend away from the channel.

7. The medical device of claim 6, wherein the slider is configured to slide into contact with the electrical lead and secure the electrical lead within the channel, wherein the cam lobe is configured to, as the rotatable member is rotated and the cam lobe engages the central portion of the slider, push on the central portion to move the slider toward the channel.

8. The medical device of claim 7, further comprising a slider protrusion on the central portion of the slider, the slider protrusion defining a slider surface parallel to the channel, the slider protrusion configured to engage the electrical lead as the rotatable member is rotated toward the center portion, and wherein the housing defining the channel configured to receive the electrical lead further defines a chamber adjacent to the channel, the chamber defining a range of motion for the slider.

9. The medical device of claim 6, further comprising a cam stop operably coupled to the first end and extending inward toward the rotatable member, parallel with the first end, the cam stop configured to contact and restrict rotation of the rotatable member when the cam lobe engages the cam stop.

10. The medical device of claim 6, further comprising a retraction member operably coupled to the second end and extending toward the rotatable member parallel to the channel, the retraction member configured to contact the cam lobe during rotation of the cam lobe in a retraction direction, wherein as the cam lobe is configured to engage the retraction member as the slider is pulled away from the channel.

11. The medical device of claim 1, wherein an upper surface of the rotatable member defines a hexagonal indentation in a surface of the rotatable member orthogonal to the longitudinal axis, the hexagonal indentation configured to receive a distal end of a hex key to rotate the rotatable member.

12. The medical device of claim 1, wherein the cam lobe extends out from the rotatable member at an acute angle.

13. The medical device of claim 1, wherein the cam lobe surface has a length which is between 75-85% of a distance between the longitudinal axis and the cam lobe surface.

14. A medical system, comprising:
a medical device comprising:
a housing defining a first channel configured to receive a first electrical lead; and
a first rotatable member defining a first longitudinal axis about which the first rotatable member is configured to rotate, wherein the first rotatable member defines:
an outer surface having a first radius; and
a first cam lobe extending farther from the longitudinal axis than the first radius of the outer surface, the first cam lobe defining a first cam lobe surface parallel to the longitudinal axis, wherein the first cam lobe surface defines a first portion at a first radius from the longitudinal axis, a second portion at a second radius from the longitudinal axis, and a midsection at a midsection radius from the longitudinal axis and between the first portion and the second portion, wherein the first radius and the second radius are larger than the midsection radius, and wherein the first cam lobe surface of the first cam lobe is configured to retain the first electrical lead within the first channel.

15. The medical system of claim 14, further comprising a second channel defined by the housing configured to receive a second electrical lead and a second rotatable member defining a second longitudinal axis about which the second rotatable member is configured to rotate, wherein the second rotatable member defines:
a second outer surface having a second radius; and
a second cam lobe extending farther from the second longitudinal axis than the second radius of the second outer surface, the second cam lobe defining a second cam lobe surface parallel to the second longitudinal axis, wherein the second cam lobe surface comprises a third portion defining a third radius from the second longitudinal axis, a fourth portion defining a fourth radius from the second longitudinal axis, and a second midsection at a second midsection radius from the longitudinal axis and between the third portion and the fourth portion, wherein the third radius and the fourth radius are larger than the second midsection radius, and wherein the second cam lobe surface of the second cam lobe is configured to retain the second electrical lead within the second channel.

16. The medical system of claim 15, further comprising a first slider at least partially encompassing the first rotatable member; wherein the first slider is slidably mounted and configured to slide toward the first channel as the first rotatable member rotates the first cam lobe towards a central portion of the first slider, and wherein the central portion is parallel with the first channel.

17. The medical system of claim 16, further comprising a retraction member of the first slider, the retraction member located opposite of the central portion across from the first rotatable member and parallel to the central portion, wherein when the first cam lobe is configured to engage the retraction member as the first cam lobe is rotated away from the central portion to move the slider away from the first channel.

18. The medical system of claim 14, further comprising a stimulation generator configured to generate electrical stimulation deliverable via one or more electrodes of the electrical lead.

19. A medical device comprising:
a housing defining a channel configured to receive an electrical lead and defining a chamber adjacent to the channel;
a rotatable member located within the chamber, the rotatable member defining a longitudinal axis about which the rotatable member is configured to rotate, wherein the rotatable member has an outer surface having a first radius and a cam lobe extending farther from the first radius of the outer surface, the cam lobe defining a first cam lobe surface parallel to the longitudinal axis, wherein the cam lobe surface comprises a first portion at a first radius from the longitudinal axis, a second portion at a second radius from the longitudinal axis, and a midsection at a midsection radius from the longitudinal axis and between the first portion and the second portion, wherein the first radius and the second radius are larger than the midsection radius;
a slider having a central portion parallel with the cam lobe, the central portion terminating in a first end and a second end where both the first end and the second end extend away from the channel, wherein the slider is configured to slide into contact with the electrical lead and secure the electrical lead within the channel, wherein the cam lobe is configured to, as the rotatable member is rotated and the cam lobe engages the central portion of the slider, push on the central portion to move the slider toward the channel;
a slider protrusion on the central portion of the slider, the slider protrusion defining a slider surface parallel to the channel, the slider protrusion configured to engage the electrical lead as the rotatable member is rotated toward the center portion;
a cam stop operably coupled to the first end and extending inward toward the rotatable member, parallel with the first end, the cam stop configured to contact and restrict rotation of the rotatable member when the cam lobe engages the cam stop; and
a retraction member operably coupled to the second end and extending toward the rotatable member parallel to the channel, the retraction member configured to contact the cam lobe during rotation of the cam lobe in a retraction direction, wherein as the cam lobe is configured to engage the retraction member as the slider is pushed away from the channel.

20. The medical device of claim 19, wherein the longitudinal axis is one of parallel to or perpendicular to the channel.

* * * * *